(12) United States Patent
Peglion et al.

(10) Patent No.: US 7,612,061 B2
(45) Date of Patent: Nov. 3, 2009

(54) PIPERAZINE COMPOUNDS

(75) Inventors: Jean-Louis Peglion, Le Vesinet (FR); Aimee Dessinges, Ruiel-Malmaison (FR); Bertrand Goument, Viroflay (FR); Mark Millan, Le Pecq (FR); Clotilde Mannoury La Cour, Paris (FR)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 12/291,485

(22) Filed: Nov. 10, 2008

(65) Prior Publication Data

US 2009/0076030 A1    Mar. 19, 2009

Related U.S. Application Data

(62) Division of application No. 11/395,747, filed on Mar. 31, 2006, now Pat. No. 7,465,733.

(30) Foreign Application Priority Data

Apr. 8, 2005   (FR) .................................. 05 03512

(51) Int. Cl.
*A61K 31/551* (2006.01)
*C07D 295/081* (2006.01)

(52) U.S. Cl. ...................................... 514/218; 540/575
(58) Field of Classification Search ................. None
See application file for complete search history.

(56) References Cited

U.S. PATENT DOCUMENTS 6,136,824 A    10/2000    MacLeod et al.

OTHER PUBLICATIONS

T. Rickmans, et al., "Dual NK(1) Antagonists—Serotonin Reuptake Inhibitors as Potential Antidepressants. Part 2: Sar and Activity of Benzyloxyphenethyl Piperazine Derivatives" Bioorganic & Medicinal Chemistry Letters, vol. 12, No. 21, pp. 3195-3198, Nov. 4, 2002.

K. Bhandari, et al., "Synthesis of 1-amino-1,2,3,4-tetrahydronaphthalen-2-olis via epoxide ring opening as possible antidepressant and anorexigenic agents" Indian Journal of Chemistry, vol. 39 b, pp. 468-471, Jun. 2000.

Preliminary Search Report: FR 0503512—Feb. 7, 2006.

*Primary Examiner*—Emily Bernhardt
(74) *Attorney, Agent, or Firm*—Hueschen and Sage

(57) ABSTRACT

A compound selected from those of formula (I):

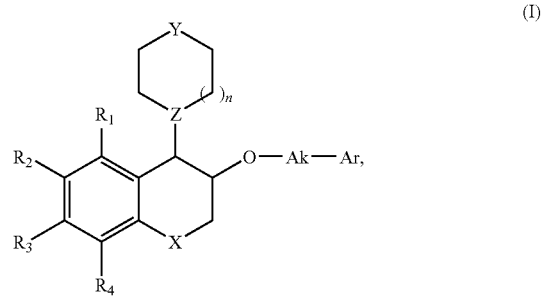

wherein:
$R_1$, $R_2$, $R_3$ and $R_4$, which may be the same or different, each represent an atom or group selected from hydrogen, halogen, alkyl, alkoxy, phenyl and cyano, X represents a bond, an oxygen atom or a group selected from —$(CH_2)_m$—, —$OCH_2$— and —$NR_5$—, wherein m represents 1 or 2, and $R_5$ is as defined in the description, Y represents an oxygen atom or a group selected from $NR_7$ and $CHR_8$, wherein $R_7$ and $R_8$ are as defined in the description, Z represents a nitrogen atom or a CH group,
n represents 1 or 2,
Ak represents an alkylene chain,
Ar represents an aryl or heteroaryl group,
its optical isomers, and addition salts thereof with a pharmaceutically acceptable acid.

Medical products containing the same which are useful in the treatment of conditions requiring a serotonin reuptake inhibitor and/or $NK_1$ antagonist.

6 Claims, No Drawings

PIPERAZINE COMPOUNDS

The present invention relates to piperazine compounds, to a process for their preparation and to pharmaceutical compositions containing them, and also to their use as serotonin reuptake inhibitors.

By virtue thereof, they are useful in the treatment of depressive states (Goodnick and Goldstein, *J Psychopharmacol* 1998, 12 (Suppl B):S55-S87; Cheer and Goa, *Drugs* 2001, 61:81-110; MacQueen et al., *CNS Drug Rev* 2001, 7:1-24; Wagstaff et al., *Drugs* 2002, 62:655-703), anxiety states such as generalised anxiety, panic attacks and phobias (Feighner, *J Clin Psychiatry* 1999, 60 (Suppl 22):18-22; Bakker et al., *Int clin Psychopharmacol* 2000, 15 (Suppl 2):S25-S30; Davidson, *Int Clin Psychopharmacol* 2000, 15 (suppl 1):S13-S17; Schneier, *J Clin Psychiatry* 2001, 62 (Suppl 1):43-48), the harmful effect of stress whether psychological (Marona-Lewicka and Nichols, *Stress* 1997, 2:91-100; Mar et al., *Pharmacol Biochem Behav* 2002, 73:703-712; Will et al., *Mol Psychiatry* 2003, 8:925-932; Ballenger, *J Clin Psychiatry* 2004, 65:1696-1707) or neurotoxic (Malberg and Duman, *Neuropsychopharmacology* 2003, 28:1562-1571; Santarelli et al., *Science* 2003, 301:805-809; Czeh et al., *Neuropsychopharmacology* 2005, 30:67-79; Malberg and Schechter, *Curr Pharm Des* 2005, 11:145-155), impulsive states such as "ODC" or obsessive-compulsive behaviour disorders (Njung'e and Handley, *Br J Pharmacol* 1991, 104:105-112; Ichimaru et al., *Jpn J Pharmacol* 1995, 68:65-70; Pigott and Seay, *J Clin Psychiatry* 1999, 60:101-106; Vythilingum et al., *Int Clin Psychopharmacol* 2000, 15 (Suppl 2)S7-S13), aggressive states (Knutson et al., *Am J Psychiatry* 1998, 155: 373-379; Lanctot et al., *Neuropsychopharmacology* 2002, 27:646-654; New et al., *Psychopharmacology* 2004, 176: 451-458), obesity and appetite disorders such as bulimia (Proietto et al., *Expert Opin Investig Drugs* 2000, 9:1317-1326; Ljung et al., *J Intern Med* 2001, 250:219-224; Appolinario et al., *CNS Drugs* 2004, 18:629-651; Appolinario and McElroy, *Curr Drug Targets* 2004, 5:301-307), pain states (Aragona et al., *Eur J Pain* 2005, 9:33-38; Millan et al., *Neuropharmacology* 2002, 42:677-684; Duman et al., *J Pharmacol Sci* 2004, 94:161-165; Otsuka et al., *J Anesth* 2004, 15:154-158); and, in relation to those entities, disorders of behaviour and of neuronal degeneration associated with dementia and other disorders of aging (Lyketos et al., *Am J Psychiatry* 2000, 157:1686-1689; Lanctot et al., *J Neuropsychiatry Clin Neurosci* 2001, 13:5-21; Lanctot et al., *Neuropsychopharmacology* 2002, 27:646-654; Pollock et al., *Am J Psychiatry* 2002, 159:460-465).

Furthermore, most of the compounds of the present invention are also active as neurokinin $NK_1$ antagonists.

By virtue thereof, they are also useful in the treatment of depressive states (Rupniak et al., *Behav Pharmacol* 2001, 12:497-508; Rupniak et al., *Neuropharmacology* 2003, 44:516-523; Kramer et al., *Neuropsychopharmacology* 2004, 29:385-392; Dableh et al., *Eur J Pharmacol* 2005, 507:99-105), anxiety states such as generalised anxiety, panic attacks and phobias (Rupniak et al, *Behav Pharmacol* 2001, 12:497-508; Santarelli et al., *Proc Natl Acad Sci USA* 2001, 98:1912-1927; Varty et al., *Neuropsychopharmacology* 2002, 27:371-379; Rupniak and Kramer, *Neuropsychopharmacology* 2002, 13:169-177), the harmful effect of stress whether psychological (Ballard et al., *Eur J Pharmacol* 2001, 412:255-264; Rupniak and Kramer, *Neuropsychopharmacology* 2002, 13:169-177; Spooren et al., *Eur J Pharmacol* 2002, 435:161-170; Steinberg et al., *J Pharmacol Exp Ther* 2002, 303:1180-1188) or neurotoxic (Van der Hart et al., *Mol Psychiatry* 2002, 7:933-941; Morcuende et al., *Eur J Neurosci* 2003, 18:1828-1836; Guest et al., *Brain Res* 2004, 1002:1-10; Czeh et al., *Neuropsychopharmacology* 2005, 30:67-79), impulsive states such as obsessive-compulsive behaviour disorders (Culman et al., *Br J Pharmacol* 1995, 114:1310-1316; Tschöpe et al., *Br J Pharmacol* 1992, 107:750-755; Rupniak et al., *Behav Pharmacol* 2001, 12:497-508; Millan et al., *Neuropharmacology* 2002, 42:677-684), aggressive states (Siegel and Schubert, *Rev Neurosci* 1995, 6:47-61; De Felipe et al., *Nature* 1998, 392:394-397; Rupniak et al., *Behav Pharmacol* 2001, 12:497-508), but also drug abuse (Murtra et al., *Nature* 2000, 405:180-183; Ripley et al., *Neuropharmacology* 2002, 43:1258-1268; Gadd et al., *J Neurosci* 2003, 23:8271-8280), psychotic states (Zachrisson et al., *Eur Neuropsychopharmacol* 2000, 10:355-363) and extrapyramidal motor effects caused by antipsychotics (Anderson et al., *J Pharmacol Exp Ther* 1995, 274:928-936, Steinberg et al., *J Pharmacol Exp Ther* 2002, 303:1180-1188), sexual dysfunctions (Priest et al., *Brain Res Mol Brain Res* 1995, 28:61-71; Daniels et al., *Neurosci Lett* 2003, 338:111-114; Kramer et al., *Science* 1998, 281:1640-1644; Kramer et al., *Neuropsychopharmacology* 2004, 29:385-392), disturbances of chronobiological rhythms such as circadian rhythms (Shibata et al., *Brain Res* 1992, 597:257-263; Challet et al., *Brain Res* 1998, 800:32-39; Challet et al., *Neuropharmacology* 2001, 40:408-415; Gannon et al., *Neuropharmacology*, in press), pain (Seguin et al., *Pain* 1995, 61:325-343; De Felipe et al., *Nature* 1998, 392:394-397; Sanger, *Br J Pharmacol* 2004, 141:1303-1312) and/or inflammation (Seabrook et al., *Eur J Pharmacol* 1996, 317:129-135; Holzer, *Digestion* 1998, 59:269-283; Joos and Pauwels, *Curr Opin Pharmacol* 2001, 1:235-241; Sanger, *Br J Pharmacol* 2004, 141:1303-1312), nausea and other gastrointestinal disorders (McAllister and Pratt *Eur J Pharmacol* 1998, 353:141-148; Gardner et al., *Regulatory Peptides* 1996, 65:45-53; Patel and Lindley, *Expert Opin. Pharmacother* 2003, 4:2279-2296; Sanger, *Br J Pharmacol* 2004, 141:1303-1312); and, in relation to those entities, disorders of behaviour and of neuronal degeneration associated with dementia and other disorders of aging (Raffa, *Neurosci Biobehav Rev* 1998, 22:789-813).

The compounds that are active both on $NK_1$ receptors and on serotonin (5-HT) reuptake sites should have complementary and synergistic mechanisms for controlling impulsive, aggressive, painful and, above all, depressive states. It has moreover been shown that blocking $NK_1$ receptors potentiates the influence of 5-HT reuptake inhibitors on serotoninergic transmission: because of that fact, such compounds should bring about more rapid and more robust antidepressant effects (Guiard et al., *J Neurochem* 2004, 89:54-63; Froger et al., *J Neurosci* 2001, 21:8188-8197). The rapid anxiolytic effects of $NK_1$ antagonists should, moreover, be complementary to the anxiolytic effects of 5-HT reuptake inhibitors, which are expressed after long-term treatment. With regard to the anxiogenic effects brought about by 5-HT at the start of treatment (Bagdy et al., *Int J Neuropsychopharmacol* 2001, 4:399-408), these should be prevented by the $NK_1$ antagonist properties (Ballard et al., *Eur J Pharmacol* 2001, 412:255-264; Rupniak et al., *Neuropharmacology* 2003, 44:516-523). As far as the other undesirable effects associated with 5-HT reuptake blocking are concerned, such as emetic effects (Goldstein and Goodnick, *J Psychopharmacol* 1998, 12 (Suppl B):S55-S87; Edwards and Anderson, *Drugs* 1999, 57:507-533; Waugh and Goa, *CNS Drugs* 2003, 17:343-362) and the causation of sexual dysfunctions (Goldstein and Goodnick, *J Psychopharmacol* 1998, 12 (Suppl B):S55-S87; Montgomery et al., *J Affect disord* 2002, 69:119-

140; Hirschfeld, *J Clin Psychiatry* 2003, 64 (Suppl 18):20-24), $NK_1$ antagonists should also be capable of counteracting those effects.

Consequently, the compounds that are both $NK_1$ antagonists and serotonin reuptake inhibitors should have therapeutic advantages over compounds that interact with only one or other of those two targets.

More specifically, the present invention relates to compounds of formula (I):

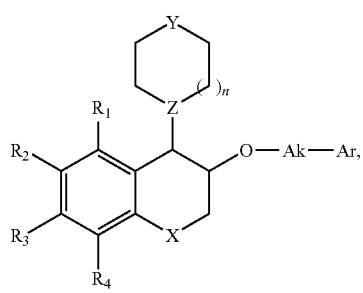

(I)

wherein:
 $R_1$, $R_2$, $R_3$ and $R_4$, which may be the same or different, each represent an atom or group selected from H, halogen, linear or branched $C_1$-$C_6$alkyl, linear or branched $C_1$-$C_6$alkoxy, phenyl and cyano,
 X represents a bond, an oxygen atom or a group selected from —$(CH_2)_m$—, —$OCH_2$— and —$NR_5$—,
  m represents 1 or 2,
  $R_5$ represents a hydrogen atom or a group selected from linear or branched $C_1$-$C_6$alkyl, $COR_6$ and $CO_2R_6$,
  $R_6$ represents a linear or branched $C_1$-$C_6$alkyl group,
 Y represents an oxygen atom or a group selected from $NR_7$ and $CHR_8$,
  $R_7$ represents a hydrogen atom or a group selected from $COR_9$ and linear or branched $C_1$-$C_6$alkyl, the alkyl group being optionally substituted by a 5-oxo-4,5-dihydro-1H-1,2,4-triazol-3-yl or 2,3-dihydro-1,4-benzodioxin-2-yl group,
  $R_9$ represents a group selected from linear or branched $C_1$-$C_6$alkyl, aryl and heteroaryl,
  $R_8$ represents a hydrogen atom or an amino group optionally substituted by one or two linear or branched $C_1$-$C_6$alkyl groups,
 Z represents a nitrogen atom or a CH group,
 n represents 1 or 2,
 Ak represents a linear or branched $C_1$-$C_6$alkylene chain,
 Ar represents an aryl or heteroaryl group, to their optical isomers, and also to addition salts thereof with a pharmaceutically acceptable acid.

Optical isomers are understood to mean enantiomers and diastereoisomers.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid, dibenzoyltartaric acid.

An aryl group is understood to mean phenyl, biphenylyl or naphthyl, each of those groups optionally being substituted by one or more identical or different groups selected from halogen, linear or branched $C_1$-$C_6$alkyl, linear or branched $C_1$-$C_6$alkoxy, hydroxy, cyano, linear or branched $C_1$-$C_6$trihaloalkyl and linear or branched $C_1$-$C_6$trihaloalkoxy.

A heteroaryl group is understood to mean an aromatic mono- or bi-cyclic 5- to 12-membered group containing one, two or three hetero atoms selected from oxygen, nitrogen and sulphur, it being understood that the heteroaryl group may optionally be substituted by one or more identical or different groups selected from halogen, linear or branched $C_1$-$C_6$alkyl, linear or branched $C_1$-$C_6$alkoxy, hydroxy, cyano and linear or branched $C_1$-$C_6$trihaloalkyl.

X preferably represents a bond, an oxygen atom or a group selected from —$OCH_2$— and —$(CH_2)_m$— wherein m represents 1 or 2.

Y preferably represents NH.

Z preferably represents a nitrogen atom.

n preferably represent 1.

Ar preferably represents an aryl group.

Preferred compounds according to the invention are:
 trans-1-{2-[(3,5-dibromobenzyl)oxy]-2,3-dihydro-1H-inden-1-yl}piperazine, its enantiomers, and also addition salts thereof with a pharmaceutically acceptable acid,
 trans-1-{3-[(3,5-dibromobenzyl)oxy]-3,4-dihydro-2H-chromen-4-yl}piperazine, its enantiomers, and also addition salts thereof with a pharmaceutically acceptable acid,
 trans-1-{6-[(3,5-dibromobenzyl)oxy]-6,7,8,9-tetrahydro-5H-benzo[7]annulen-5-yl}-piperazine, its enantiomers, and also addition salts thereof with a pharmaceutically acceptable acid,
 trans-1-{2-[(3,5-dibromobenzyl)oxy]-1,2,3,4-tetrahydronaphth-1-yl}piperazine, its enantiomers, and also addition salts thereof with a pharmaceutically acceptable acid,
 trans-1-{2-[(3,5-dibromobenzyl)oxy]-1,2,3,4-tetrahydronaphth-1-yl}-1,4-diazepane, its enantiomers, and also addition salts thereof with a pharmaceutically acceptable acid,
 1-{(1S,2R)-2-[(3,5-dibromobenzyl)oxy]-2,3-dihydro-1H-inden-1-yl}piperazine, its enantiomers, and also addition salts thereof with a pharmaceutically acceptable acid,
 1-[(1S,2R)-2-[(3,5-difluorobenzyl)oxy]-2,3-dihydro-1H-inden-1-yl]piperazine, its enantiomers, and also addition salts thereof with a pharmaceutically acceptable acid,
 1-[(1S,2R)-2-[(3,5-dimethylbenzyl)oxy]-2,3-dihydro-1H-inden-1-yl]piperazine, its enantiomers, and also addition salts thereof with a pharmaceutically acceptable acid,
 trans-1-{3-[(3,5-dichlorobenzyl)oxy]-3,4-dihydro-2H-chromen-4-yl}piperazine, its enantiomers, and also addition salts thereof with a pharmaceutically acceptable acid,
 trans-1-{3-[3-fluoro-5-(trifluoromethyl)benzyloxy]-3,4-dihydro-2H-chromen-4-yl}-piperazine, its enantiomers, and also addition salts thereof with a pharmaceutically acceptable acid,
 and trans-1-{3-(3-chloro-5-fluorobenzyloxy)-3,4-dihydro-2H-chromen-4-yl}piperazine, its enantiomers, and also addition salts thereof with a pharmaceutically acceptable acid.

The invention relates also to a process for the preparation of compounds of formula (I), starting from the compound of formula (Va), of relative configuration trans:

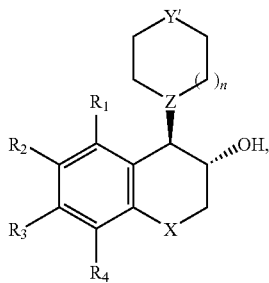

(Va)

wherein $R_1$, $R_2$, $R_3$, $R_4$, X, n and Z are as defined hereinbefore, and Y' represents an oxygen atom or a group selected from $NP_1$ and $CHR'_8$, wherein $R'_8$ represents a hydrogen atom or a group $NHP_1$, and $P_1$ represents a protecting group for the amine function, which compound of formula (Va) is reacted, when it is desired to obtain compounds of formula (I) of relative configuration trans, with a compound of formula (VI):

G-Ak-Ar  (VI), wherein Ak and Ar are as defined for formula (I), and G represents a leaving group such as, for example, a halogen atom or a p-toluenesulphonate, trifluoromethanesulphonate or methanesulphonate group, to yield the compound of formula (VIIa), of relative configuration trans:

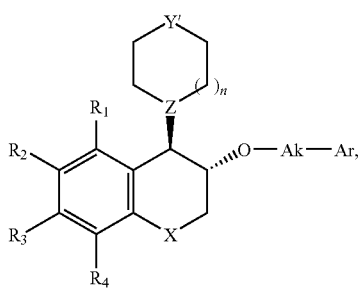

(VIIa)

wherein $R_1$, $R_2$, $R_3$, $R_4$, X, n, Y', Z, Ak and Ar are as defined hereinbefore, which is deprotected when Y' contains a protecting group $P_1$ as defined hereinbefore and is then alkylated, when it is desired to obtain compounds wherein Y represents a group $NR_7$ wherein $R_7$ is other than a hydrogen atom, to yield compounds of formula (Ia), a particular case of the compounds of formula (I), which are of relative configuration trans:

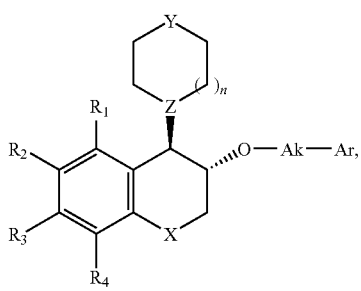

(Ia)

wherein $R_1$, $R_2$, $R_3$, $R_4$, X, n, Y, Z, Ak and Ar are as defined for formula (I), or which compound of formula (Va) is oxidised, when it is desired to obtain compounds of formula (I) of relative configuration cis, to yield the racemic compound of formula (VIII):

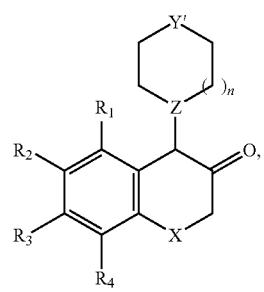

(VIII)

wherein $R_1$, $R_2$, $R_3$, $R_4$, X, Z, n and Y' are as defined hereinbefore, which is reduced to the corresponding alcohol, the diastereoisomers of which are separated, and the isomer of formula (Vb), of relative configuration cis, is isolated:

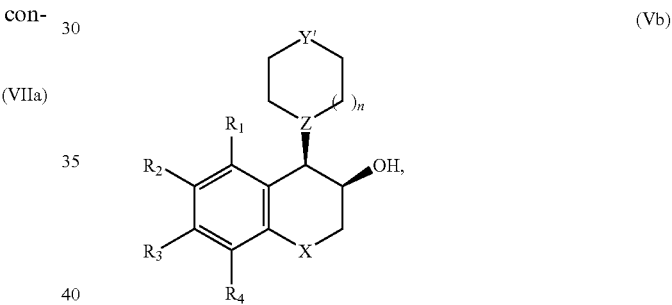

(Vb)

wherein $R_1$, $R_2$, $R_3$, $R_4$, X, Y', Z and n are as defined hereinbefore, which is reacted with a compound of formula (VI) as defined hereinbefore to yield the compound of formula (VIIb), of relative configuration cis:

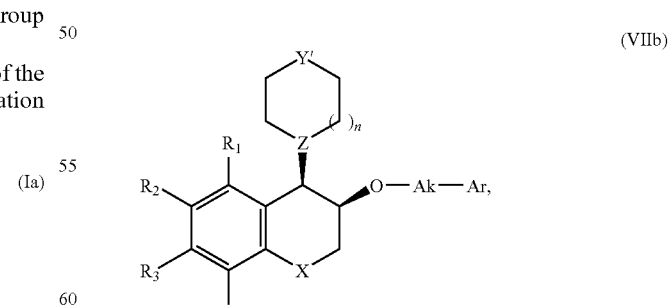

(VIIb)

wherein $R_1$, $R_2$, $R_3$, $R_4$, X, n, Y', Z, Ak and Ar are as defined hereinbefore, which is deprotected when Y' contains a protecting group $P_1$ as defined hereinbefore and is then alkylated, when it is desired to obtain compounds wherein Y represents a group $NR_7$ wherein $R_7$ is other than a hydrogen atom, to yield compounds of formula (Ib), a particular case of the compounds of formula (I), which are of relative configuration cis:

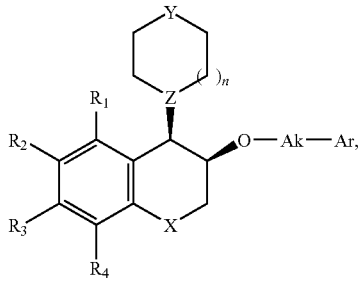

(Ib)

wherein $R_1$, $R_2$, $R_3$, $R_4$, X, Y, Z, n, Ak and Ar are as defined for formula (I), which compounds of formulae (Ia) and (Ib) may be purified according to a conventional purification technique, are separated, when desired, into their optical isomers and are converted, when desired, into their addition salts with a pharmaceutically acceptable acid.

The compounds of formula (Ic), a particular case of compounds of formula (I) wherein Ak represents a group —CH(CH$_3$)—:

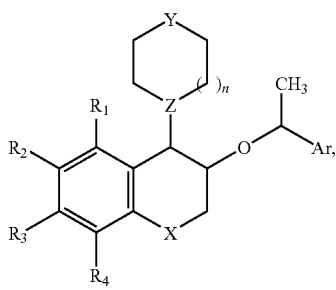

(Ic)

wherein $R_1$, $R_2$, $R_3$, $R_4$, X, n, Y, Z and Ar are as defined for formula (I), may also be prepared by condensation of the alcohol of formula (Va) or (Vb) with an acid of formula (IX):

   (IX), wherein Ar is as defined for formula (I), to yield the ester of formula (X):

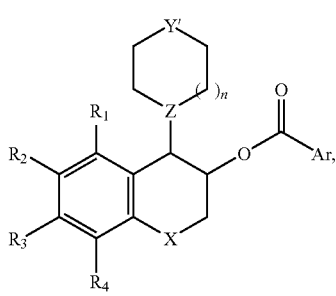

(X)

wherein $R_1$, $R_2$, $R_3$, $R_4$, X, n, Y', Z and Ar are as defined hereinbefore, which is reacted with bis(cyclopentadienyl)dimethyltitanium, to yield the compound of formula (XI):

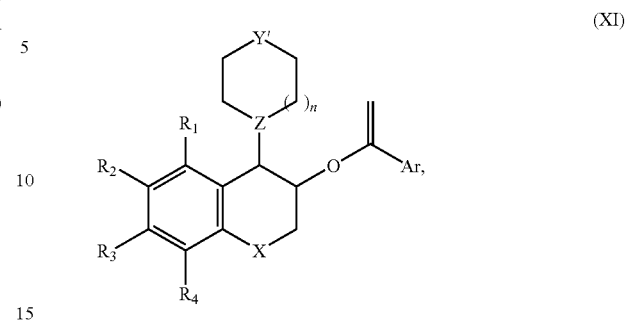

(XI)

wherein $R_1$, $R_2$, $R_3$, $R_4$, X, n, Y', Z and Ar are as defined hereinbefore, which is hydrogenated to yield the compound of formula (XII):

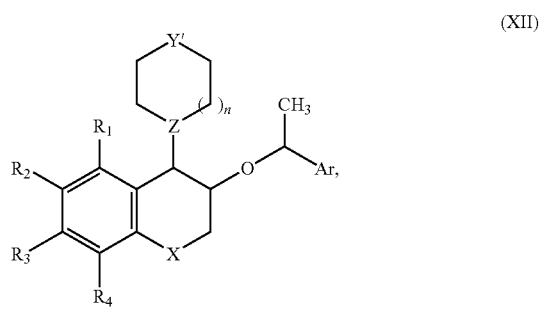

(XII)

wherein $R_1$, $R_2$, $R_3$, $R_4$, X, n, Y', Z and Ar are as defined hereinbefore, which is separated into its isomers and is then deprotected when Y' contains a protecting group $P_1$ as defined hereinbefore and alkylated, when it is desired to obtain compounds wherein Y represents a group $NR_7$ wherein $R_7$ is other than a hydrogen atom, to yield compounds of formula (Ic).

The compounds of formula (Va$_1$), a particular case of compounds of formula (Va) wherein Z represents a nitrogen atom, may be prepared starting from the compound of formula (II):

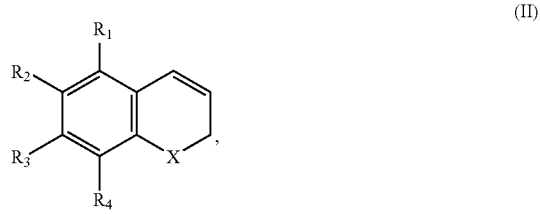

(II)

wherein $R_1$, $R_2$, $R_3$, $R_4$ and X are as defined for formula (I), which is oxidised into the compound of formula (III):

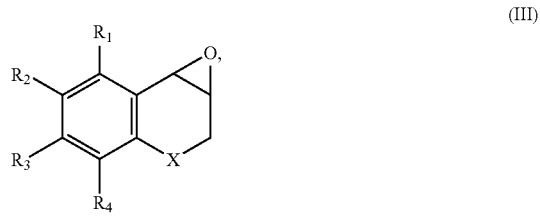

(III)

wherein $R_1$, $R_2$, $R_3$, $R_4$ and X are as defined hereinbefore,
which is reacted with the compound of formula (IV):

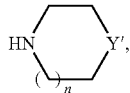
(IV)

wherein n is as defined for formula (I) and Y' is as defined hereinbefore,
to yield the compound of formula (Va$_1$):

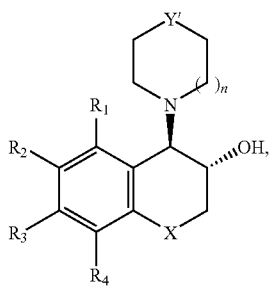
(Va$_1$)

wherein $R_1$, $R_2$, $R_3$, $R_4$, X, Y' and n are as defined hereinbefore.

The compounds of formula (Va$_2$), a particular case of the compounds of formula (Va) wherein Z represents a CH group, n represents 1 and Y' represents a NP$_1$ group, may be prepared starting from the compound of formula (XIII):

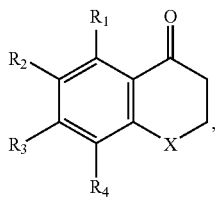
(XIII)

wherein $R_1$, $R_2$, $R_3$, $R_4$ and X are as defined hereinbefore,
which is reacted with 4-pyridyllithium to yield the compound of formula (XIV):

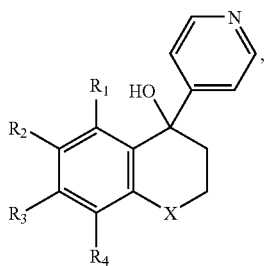
(XIV)

wherein $R_1$, $R_2$, $R_3$, $R_4$ and X are as defined hereinbefore,
which is dehydrated to yield the compound of formula (XV):

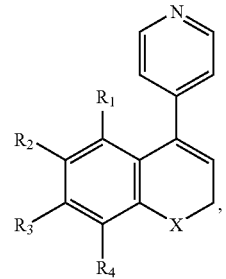
(XV)

wherein $R_1$, $R_2$, $R_3$, $R_4$ and X are as defined hereinbefore,
which is reacted with Oxone to yield the compound of formula (XVI):

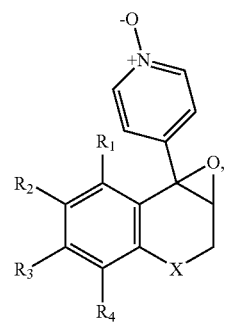
(XVI)

wherein $R_1$, $R_2$, $R_3$, $R_4$ and X are as defined hereinbefore,
which is reacted with a reducing agent to yield the compound of formula (XVII):

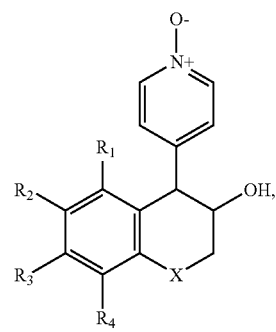
(XVII)

wherein $R_1$, $R_2$, $R_3$, $R_4$ and X are as defined hereinbefore,
which is subjected to a catalytic hydrogenation reaction to yield the compound of formula (XVIII):

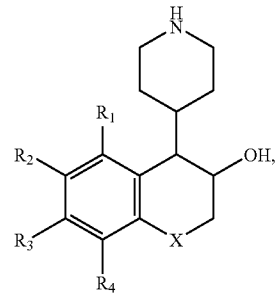
(XVIII)

wherein $R_1$, $R_2$, $R_3$, $R_4$ and X are as defined hereinbefore, the cis and trans isomers of which are separated, the amine function of the trans isomer of which is protected to yield the compound of formula (Va₂), of relative configuration trans:

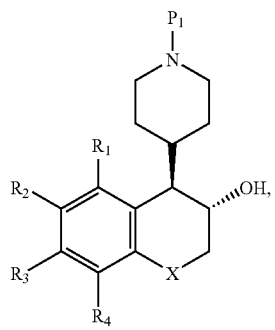

(Va₂)

wherein $R_1$, $R_2$, $R_3$, $R_4$ and X are as defined hereinbefore.

The compounds of the present invention are serotonin reuptake inhibitors, and most of them are also $NK_1$ antagonists. They are useful as medicaments in the treatment of depressive states, anxiety states, impulsive disorders, aggressive behaviours, drug abuse, obesity and appetite disorders, pain and inflammation, dementias, psychotic states, disturbances of chronobiological rhythms, nausea and gastrointestinal disorders.

The present invention relates also to pharmaceutical compositions comprising, as active ingredient, a compound of formula (I), or an addition salt thereof with a pharmaceutically acceptable acid, in combination with one or more pharmaceutically acceptable, inert, non-toxic excipients or carriers.

Among the pharmaceutical compositions according to the invention there may be mentioned more especially those that are suitable for oral, parenteral (intravenous, intramuscular or subcutaneous), per- or trans-cutaneous, nasal, rectal, perlingual, ocular or respiratory administration, and especially tablets or dragées, sublingual tablets, gelatin capsules, capsules, suppositories, creams, ointments, dermal gels, injectable or drinkable preparations, aerosols, eye drops and nose drops.

The useful dosage varies according to the age and weight of the patient, the administration route, the nature and severity of the disorder, and the administration of any associated treatments and ranges from 0.5 to 500 mg per day in one or more administrations.

The Examples that follow illustrate the invention. The starting materials used are known products or are prepared according to known procedures. The various Preparations yield synthesis intermediates that are of use in preparation of the compounds of the invention.

The structures of the compounds described in the Examples were determined according to customary spectrophotometric techniques (infra-red, nuclear magnetic resonance, mass spectrometry).

The melting points were determined either on a Kofler bench (BK) or on a hot-plate under a microscope (MK).

PREPARATION A

6-Bromo-1,2-dihydronaphthalene

Step A: 7-Bromo-1,2,3,4-tetrahydronaphth-1-ol

To 9.5 g of 7-bromo-3,4-dihydronaphthalen-1(2H)-one (42 mmol), prepared according to the method described in Synth. Comm. 1994, 2777, dissolved in 100 ml of ethanol, there are added, at 0° C. and in two portions, 0.8 g of sodium borohydride (21 mmol). The reaction mixture is then allowed to come back up to ambient temperature over 30 minutes, and then the ethanol is evaporated off. The residue is taken up in 100 ml of toluene and 100 ml of water. After separation, the aqueous phase is extracted with 50 ml of toluene. The toluene phases are combined, washed with a saturated aqueous solution of sodium chloride and are then evaporated to yield 7-bromo-1,2,3,4-tetrahydronaphth-1-ol in the form of an oil.

Step B: 6-Bromo-1,2-dihydronaphthalene

A solution of 8.6 g of the compound obtained in the Step above (37.9 mmol) in 200 ml of toluene is heated to 100° C. At that temperature there is added dropwise, over one hour, a solution of 0.3 g of para-toluenesulphonic acid (1.2 mmol) dissolved in 400 ml of toluene. The reaction mixture is subsequently cooled to 25° C. and then hydrolysed using 100 ml of water. The organic phase is extracted and then dried, filtered and evaporated to yield 6-bromo-1,2-dihydronaphthalene in the form of an oil.

PREPARATION B

7-Bromo-2,3-dihydro-1-benzoxepin

Step A: 4-[5-Bromo-2-(but-3-en-1-yloxy)phenyl]-4-hydroxybutan-2-one

To 300 ml of acetone there are added 10 g of 5-bromo-2-hydroxybenzaldehyde (49.7 mmol), 13.7 g of potassium carbonate (99.5 mmol) and 10.1 ml of 4-bromobut-1-ene (99.5 mmol); the reaction mixture is then heated at reflux for 36 hours before being cooled, filtered and evaporated to dryness to yield 4-[5-bromo-2-(but-3-en-1-yloxy)phenyl]-4-hydroxybutan-2-one in the form of an oil.

Step B: 4-Bromo-1-(but-3-en-1-yloxy)-2-vinylbenzene

To 90 ml of anhydrous tetrahydrofuran there are added 1.6 g of 60% sodium hydride in oil (39.8 mmol) and then, at 0° C. and all at once, 10.67 g of methyl(triphenyl)phosphonium bromide (29.9 mmol).

The mixture is allowed to come back up to ambient temperature and is stirred for 30 minutes at 25° C. A solution of 8 g of the compound obtained in the Step above (24.9 mmol) in 30 ml of anhydrous tetrahydrofuran is then added dropwise to the reaction mixture, at ambient temperature. An exothermic reaction from 25° C. to 35° C. is observed over 45 minutes. Stirring is carried out for a further 2 hours at ambient temperature; the reaction mixture is then filtered and the filtrate is poured into a mixture of 100 ml of ethyl acetate, 200 ml of a saturated aqueous solution of sodium chloride and 50 g of ice. After extraction with ethyl acetate, the combined organic phases are washed with water, dried, filtered and evaporated to dryness. The residue obtained is purified by filtration over 100 g of silica (eluant: toluene 100%) to yield 4-bromo-1-(but-3-en-1-yloxy)-2-vinylbenzene in the form of an oil.

Step C: 7-Bromo-2,3-dihydro-1-benzoxepin 5 g of the compound obtained in the Step above (19.8 mmol) are dissolved in 500 ml of toluene, and the solution is then degassed for 30 minutes using nitrogen. 335 mg (0.39 mmol) of [1,3-bis(2,4,6-trimethylphenyl)-2-imidazolidinylidene)dichloro(phenyl-methylene)-(tricyclohexylphosphine)ruthenium], or Grubb's II catalyst, are added. The reaction mixture is then heated at 50° C. for 30 minutes; the toluene is then evaporated off and the residue obtained is purified on a column of 70 g of silica (eluant: cyclo-hexane/toluene:95/5) to yield 7-bromo-2,3-dihydro-1-benzoxepin.

EXAMPLE 1 trans-1-{2-[(3,5-Dibromobenzyl)oxy]-2,3-dihydro-1H-inden-1-yl}-piperazine dihydrochloride Step A: tert-Butyl trans-4-(2-hydroxy-2,3-dihydro-1H-inden-1-yl)piperazine-1-carboxylate 11.6 g of tert-butyl piperazine-1-carboxylate (62 mmol) and 8.2 g of indene oxide (62 mmol) are dissolved in 30 ml of acetonitrile. The reaction mixture is then heated at 60° C. overnight and evaporated to dryness. The residue obtained is purified by flash chromatography on 1 kg of silica (eluant: dichloromethane/ethanol 95/5) to yield tert-butyl trans-4-(2-hydroxy-2,3-dihydro-1H-inden-1-yl)piperazine-1-carboxylate in the form of a white meringue.

Step B: tert-Butyl trans-4-{2-[(3,5-dibromobenzyl)oxy]-2,3-dihydro-1H-inden-1-yl}-piperazine-1-carboxylate To 3 g of the compound obtained in the Step above (9.42 mmol) in 30 ml of anhydrous dimethylformamide there are added 452 mg of sodium hydride as a 60% suspension in oil (11.3 mmol, 1.2 equivalents). After stirring for 30 minutes at ambient temperature there are added 3.1 g of 3,5-dibromobenzyl bromide (9.42 mmol). A slight exothermic reaction is observed. The reaction mixture is then stirred overnight at ambient temperature, and subsequently the dimethylformamide is evaporated off. The residue obtained is taken up in dichloromethane. After washing with water, drying, filtration and evaporation, there are obtained 6 g of a residue which is purified by flash chromatography on 500 g of silica (eluant: dichloromethane/ethyl acetate 90/10) to yield tert-butyl trans-4-{2-[(3,5-dibromo-benzyl)oxy]-2,3-dihydro-1H-inden-1-yl}piperazine-1-carboxylate in the form of a meringue.

Step C: trans-1-{2-[(3,5-Dibromobenzyl)oxy]-2,3-dihydro-1H-inden-1-yl}piperazine dihydrochloride 3.5 g of the compound obtained in the Step above (6.18 mmol) are dissolved in 250 ml of ethyl acetate and then gaseous hydrogen chloride is bubbled through the solution. The temperature is allowed to increase to 45° C., and stirring is then carried out for 2 hours at ambient temperature. The reaction mixture is then concentrated to two-thirds and then 50 ml of ether are added. The precipitate obtained is filtered off and then dried to yield trans-1-{2-[(3,5-dibromobenzyl)oxy]-2,3-dihydro-1H-inden-1-yl}piperazine dihydrochloride in the form of a beige solid.

Melting point (MK): 154-167° C.

EXAMPLE 2

(−) isomer of trans-1-{2-[(3,5-dibromobenzyl)oxy]-2,3-dihydro-1H-inden-1-yl}piperazine dihydrochloride After reconversion to the base, the racemic compound of Example 1 is separated by preparative chiral HPLC chromatography (eluant: isopropanol/acetonitrile/diethylamine 100/900/1) on a Chiralpak AD phase. The first of the isomers thereby separated is converted into a salt using hydrochloric acid to yield the dihydrochloride of the (−) isomer of trans-1-{2-[(3,5-dibromobenzyl)oxy]-2,3-dihydro-1H-inden-1-yl}piperazine.

Melting point (MK): 117-125° C.

Optical rotation: $[\alpha]_D$=−27.86 (c=1%, MeOH, 20° C., 589 nm).

EXAMPLE 3

(+) isomer of trans-1-{2-[(3,5-dibromobenzyl)oxy]-2,3-dihydro-1H-inden-1-yl}piperazine dihydrochloride The second of the isomers separated in Example 2 is converted into a salt using hydrochloric acid to yield the dihydrochloride of the (+) isomer of trans-1-{2-[(3,5-dibromobenzyl)oxy]-2,3-dihydro-1H-inden-1-yl}piperazine.

Melting point (MK): 115-121° C.

Optical rotation: $[\alpha]_D$=+27.29 (c=1%, MeOH, 20° C., 589 nm)

EXAMPLE 4 trans-1-{3-[(3,5-Dibromobenzyl)oxy]-3,4-dihydro-2H-chromen-4-yl}piperazine dihydrochloride Step A: trans-3-Bromochroman-4-ol To 15 g of 2H-chromene (0.113 mol) dissolved in 330 ml of a mixture of tetrahydrofuran/water 50/50 there are added 22.1 g of N-bromosuccinimide (0.124 mol, 1.1 equivalents), and the mixture is then stirred for one hour at ambient temperature. The reaction mixture is then diluted with water, and subsequently extracted twice with ethyl acetate. The combined organic phases are washed with water, dried, filtered and evaporated to dryness to yield trans-3-bromochroman-4-ol in the form of a pale-yellow solid.

Melting point (BK): 96-98° C.

Step B: 1a,7b-Dihydro-2H-oxireno[c]chromene 4.4 g of potassium hydroxide pellets (78.5 mmol) are added to 10 g of the compound obtained in the Step above (43.6 mmol), dissolved in 170 ml of tetrahydrofuran and 85 ml of water. After stirring for 2 hours at 25° C., the reaction mixture is diluted with water and extracted twice with ether. The organic phases are combined and washed with water, dried, filtered and evaporated to dryness to yield 1a,7b-dihydro-2H-oxireno[c]chromene in the form of a pale-yellow oil.

Step C: tert-Butyl trans-4-(3-hydroxy-3,4-dihydro-2H-chromen-4-yl)piperazine-1-carboxylate 4.9 g of the compound obtained in the Step above (33 mmol) are treated with 6.1 g of tert-butyl piperazine-1-carboxylate (33 mmol) according to the method described in Step A of Example 1. The oil obtained is purified by flash chromatography on 500 g of silica (eluant: dichloromethane/ethanol 95/5) to yield the expected product in the form of an oil.

Step D: tert-Butyl trans-4-{3-[(3,5-dibromobenzyl)oxy]-3,4-dihydro-2H-chromen-4-yl}-piperazine-1-carboxylate 3 g of the compound obtained in the Step above (8.9 mmol) are treated according to the method described in Step B of Example 1. The oil obtained is purified by flash chromatography on 300 g of silica to yield the expected product in the form of a white meringue.

Step E: trans-1-{3-[(3,5-Dibromobenzyl)oxy]-3,4-dihydro-2H-chromen-4-yl}-piperazine dihydrochloride 2.9 g of the compound obtained in the Step above (4.97 mmol) are treated according to the method described in Step C of Example 1. The product obtained is crystallised from ether, filtered and dried to yield the expected product in the form of white crystals.

Melting point (MK): 130-135° C.

EXAMPLE 5

(−) isomer of trans-1-{3-[(3,5-dibromobenzyl)oxy]-3,4-dihydro-2H-chromen-4-yl}piperazine dihydrochloride After reconversion to the base, the racemic compound of Example 4 is separated by preparative chiral HPLC chromatography (eluant: ethanol/diethylamine 1000/1) on a Chiralpak AD phase. The first of the isomers thereby separated is converted into a salt using hydrochloric acid to yield the dihydrochloride of the (−) isomer of trans-1-{3-[(3,5-dibromobenzyl)oxy]-3,4-dihydro-2H-chromen-4-yl}piperazine.

Melting point (MK): 128-132° C.

Optical rotation: $[\alpha]_D = -40.36$ (c=1%, MeOH, 20° C., 589 nm).

EXAMPLE 6

(+) isomer of trans-1-{3-[(3,5-dibromobenzyl)oxy]-3,4-dihydro-2H-chromen-4-yl}piperazine dihydrochloride The second of the isomers separated in Example 5 is converted into a salt using hydrochloric acid to yield the dihydrochloride of the (+) isomer of trans-1-{3-[(3,5-dibromobenzyl)oxy]-3,4-dihydro-2H-chromen-4-yl}piperazine.

Melting point (MK): 126-130° C.

Optical rotation: $[\alpha]_D = +40.92$ (c=1%, MeOH, 20° C., 589 nm).

EXAMPLE 7 trans-1-{6-[(3,5-Dibromobenzyl)oxy]-6,7,8,9-tetrahydro-5H-benzo-[7]annulen-5-yl}piperazine dihydrochloride Step A: tert-Butyl trans-4-(6-hydroxy-6,7,8,9-tetrahydro-5H-benzo[7]annulen-5-yl)-piperazine-1-carboxylate The expected product is obtained according to the procedure described in Steps A, B and C of Example 4, replacing the 2H-chromene by 6,7-dihydro-5H-benzo[7]annulene.

Step B: trans-1-{6-[(3,5-Dibromobenzyl)oxy]-6,7,8,9-tetrahydro-5H-benzo[7]annulen-5-yl}piperazine dihydrochloride The expected product is obtained according to the procedure described in Steps B and C of Example 1, starting from the compound obtained in the Step above.

Melting point (MK): 126-131° C.

EXAMPLE 8 trans-1-{4-[(3,5-Dibromobenzyl)oxy]-2,3,4,5-tetrahydro-1-benzoxepin-5-yl}piperazine dihydrochloride Step A: 1a,2,3,8b-Tetrahydrooxireno[d][1]benzoxepin To 0.5 g of 2,3-dihydro-1-benzoxepin (3.42 mmol), prepared according to the method described in *J. Org. Chem.*, 1969, 34 (1), 207, dissolved in 30 ml of a mixture of ethyl acetate/water 50/50, there are added 1.44 g of sodium hydrogen carbonate (17.1 mmol) and then, over 1 hour, a solution of 2.1 g of Oxone® (3.42 mmol) in 15 ml of water. After the end of the addition, stirring is carried out for a further hour and then the organic phase is separated off. The aqueous phase is again extracted with 10 ml of ethyl acetate, and the combined organic phases are washed with water, dried, filtered and evaporated to dryness to yield the expected product in the form of an oil.

Step B: tert-Butyl trans-4-(4-hydroxy-2,3,4,5-tetrahydro-1-benzoxepin-5-yl)piperazine-1-carboxylate The expected product is obtained according to the procedure described in Step A of Example 1, starting from the compound obtained in the Step above.

Step C: trans-1-{4-[(3,5-Dibromobenzyl)oxy]-2,3,4,5-tetrahydro-1-benzoxepin-5-yl}-piperazine dihydrochloride The expected product is obtained according to the procedure described in Steps B and C of Example 1, starting from the compound obtained in the Step above.

Melting point (MK): 132-139° C.

EXAMPLE 9 trans-1-{3-[(3,5-Dibromobenzyl)oxy]-3,4-dihydro-2H-chromen-4-yl}piperidin-4-amine dihydrochloride Step A: tert-Butyl trans-[1-(3-hydroxy-3,4-dihydro-2H-chromen-4-yl)piperidin-4-yl]-carbamate To 3 g of the compound obtained in Step B of Example 4, dissolved in 45 ml of acetonitrile, there are added 4 g of tert-butyl piperidin-4-ylcarbamate (20.2 mmol). The mixture is then heated at reflux for 12 hours and subsequently evaporated to dryness. A yellow oil is obtained which is purified by flash chromatography on silica (eluant: dichloromethane/ethanol 95/5) to yield the expected product in the form of a pale-yellow meringue.

Step B: tert-Butyl trans-1-{3-[(3,5-dibromobenzyl)oxy]-3,4-dihydro-2H-chromen-4-yl}-4-piperidylcarbamate The expected product is obtained according to the procedure described in Step B of Example 1, starting from the compound obtained in the Step above.

Step C: trans-1-(3-[(3,5-Dibromobenzyl)oxy]-3,4-dihydro-2H-chromen-4-yl/piperidin-4-amine dihydrochloride The expected product is obtained according to the procedure described in Step C of Example 1, starting from the compound obtained in the Step above.

Melting point (MK): 160-165° C.

EXAMPLE 10 trans-4-{2-[(3,5-Dibromobenzyl)oxy]-1,2,3,4-tetrahydronaphth-1-yl}morpholine hydrochloride Step A: 1a,2,3,7b-Tetrahydronaphtho[1,2-b]oxirene 36.5 g of 1,2-dihydronaphthalene (280.3 mmol) are treated with Oxone® according to the method described in Step A of Example 8 to yield the expected product in the form of an oil.

Step B: trans-1-Morpholin-4-yl-1,2,3,4-tetrahydronaphth-2-ol

To 3.95 g of the compound obtained in the Step above (27.02 mmol), dissolved in 65 ml of acetonitrile, there are added 2.35 ml of morpholine (27.02 mmol), and then 185 mg of $ZnCl_2$ (1.35 mmol). After heating at reflux for 12 hours, the mixture is evaporated to dryness and the residue obtained is purified by flash chromatography on silica (dichloro-methane/ethanol 95/5) to yield the expected product in the form of a light-brown solid.

Melting point (BK): 88-90° C.

Step C: trans-4-{2-[(3,5-Dibromobenzyl)oxy]-1,2,3,4-tetrahydronaphth-1-yl}morpholine 3 g of the compound obtained in the Step above (12.85 mmol) are treated according to the method described in Step B of Example 1. An oil is obtained which is purified by flash chromatography on silica (eluant: dichloromethane) to yield the expected product in the form of an oil.

Step D: trans-4-{2-[(3,5-Dibromobenzyl)oxy]-1,2,3,4-tetrahydronaphth-1-yl}morpholine hydrochloride To 1.9 g of the compound obtained in the Step above (3.95 mmol), dissolved in 40 ml of ethyl acetate, there are added 2.96 ml of a 2M ethereal HCl solution (5.92 mmol). After filtration and drying of the crystals, the expected product is obtained.

Melting point: (MK)=175-180° C.

EXAMPLE 11 trans-1-{2-[(3,5-Dibromobenzyl)oxy]-5-methoxy-2,3-dihydro-1H-inden-1-yl}piperazine Step A: 4-Methoxy-6,6a-dihydro-1aH-indeno[1,2-b]oxirene The expected product is obtained according to the procedure described in Steps A and B of Example 4, starting from 6-methoxy-1H-indene.

Step B: tert-Butyl trans-4-{2-[(3,5-dibromobenzyl)oxy]-5-methoxy-2,3-dihydro-1H-inden-1-yl}piperazine-1-carboxylate The expected product is obtained according to the procedure described in Steps A and B of Example 1, starting from the compound obtained in the Step above.

Step C: trans-1-{2-[(3,5-Dibromobenzyl)oxy]-5-methoxy-2,3-dihydro-1H-inden-1-yl}-piperazine 1.3 g of the compound obtained in the Step above (2.17 mmol) are treated according to the method described in Step C of Example 1. After evaporation to dryness, the product obtained is taken up in water, and the aqueous phase is adjusted to pH 8 by adding sodium hydroxide solution (1N) and extracted with ether. The organic phase is washed with water, dried, filtered and evaporated to dryness. The residue obtained is crystallised from isopropyl ether. The crystals are filtered off and dried to yield the expected product.

Melting point (MK): 101-104° C.

EXAMPLE 12 trans-1-{2-[(3,5-Dibromobenzyl)oxy]-7-methoxy-1,2,3,4-tetrahydro-naphth-1-yl}piperazine dihydrochloride Step A: 2-Bromo-7-methoxy-1,2,3,4-tetrahydronaphth-1-ol 20 g of 6-methoxy-1,2-dihydronaphthalene (126 mmol) are treated according to the method described in Step A of Example 4 to yield the expected product.

Step B: tert-Butyl trans-4-(2-hydroxy-7-methoxy-1,2,3,4-tetrahydronaphth-1-yl)-piperazine-1-carboxylate To 2 g of the compound obtained in the Step above (7.78 mmol), dissolved in 30 ml of tetrahydrofuran, there are added 1.24 g of sodium hydride as a 60% suspension in oil (31.1 mmol) and stirring is carried out for 4 hours at ambient temperature. The reaction mixture is filtered. The filtrate, which contains 6-methoxy-1a,2,3,7b-tetrahydro-naphtho[1,2-b]oxirene in solution, is then reacted with 1.5 g of tert-butyl piperazine-1-carboxylate (7.78 mmol) and 5 ml of dimethylformamide. The tetrahydrofuran is distilled off from the reaction mixture, which is then heated at 110° C. for 24 hours. The mixture is cooled, poured into water and extracted with dichloromethane. The organic phase is dried and then filtered and evaporated to dryness. The residue obtained is purified by flash chromatography on silica (eluant: dichloromethane/ethanol: 98/2) to yield the expected product.

Step C: trans-1-{2-[(3,5-Dibromobenzyl)oxy]-7-methoxy-1,2,3,4-tetrahydronaphth-1-yl}piperazine dihydrochloride The expected product is obtained according to the procedure described in Steps B and C of Example 1, starting from the compound obtained in the Step above.

Melting point (MK): 175-182° C.

EXAMPLE 13 trans-1-{2-[(3,5-Dibromobenzyl)oxy]-6-methoxy-1,2,3,4-tetrahydro-naphth-1-yl}piperazine dihydrochloride Step A: 2-Bromo-6-methoxy-1,2,3,4-tetrahydronaphth-1-ol 10.8 g of 7-methoxy-1,2-dihydronaphthalene (67.4 mmol) are treated according to the method described in Step A of Example 4 to yield the expected product.

Step B: tert-Butyl trans-4-(2-hydroxy-6-methoxy-1,2,3,4-tetrahydronaphth-1-yl)-piperazine-1-carboxylate To 9.7 g of the compound obtained in the Step above (37.8 mmol), dissolved in 150 ml of tetrahydrofuran, there are added 3 g of sodium hydride as a 60% suspension in oil (75.6 mmol, 2 equivalents), and then the reaction mixture is stirred for 24 hours at ambient temperature. After filtration, the filtrate, which contains 5-methoxy-1a,2,3,7b-tetrahydronaphtho[1,2-b]oxirene in solution, is reacted with 8.4 g of tert-butyl piperazine-1-carboxylate (45.3 mmol) in 20 ml of dimethylformamide. The tetrahydrofuran is then distilled off, and the reaction mixture is subsequently heated at 110° C. for 1 hour. The reaction mixture is then cooled before being poured into water and extracted with dichloromethane. The organic phase is then dried, filtered and evaporated to dryness to yield a residue which is purified by flash chromatography on silica (eluant: dichloromethane/ethanol: 98/2) to yield the expected product.

Step C: trans-1-{2-[(3,5-Dibromobenzyl)oxy]-6-methoxy-1,2,3,4-tetrahydronaphth-1-yl}-piperazine dihydrochloride The expected product is obtained according to the procedure described in Steps B and C of Example 1, starting from the compound obtained in the Step above.

Melting point (MK): 137-150° C.

EXAMPLE 14 trans-1-{2-[(3,5-Dibromobenzyl)oxy]-5-phenyl-2,3-dihydro-1H-inden-1-yl}piperazine dihydrochloride The expected product is obtained according to the procedure of Example 4, starting from 6-phenyl-1H-indene.

Melting point (MK): 145-153° C.

EXAMPLE 15 trans-1-{2-[(3,5-Dibromobenzyl)oxy]-1,2,3,4-tetrahydronaphth-1-yl}piperazine dihydrochloride Step A: trans-2-Bromo-1,2,3,4-tetrahydronaphth-1-ol To 13.0 g (100 mmol) of dihydronaphthalene, dissolved in a mixture of 100 ml of water and 400 ml of tetrahydrofuran, at ambient temperature, there are added, all at once, 19.6 g (110 mmol) of N-bromosuccinimide and stirring is carried out for 3 hours. There are then added 200 ml of ice-cold water and 200 ml of ether; stirring is carried out and the phases are separated. The aqueous phase is extracted with 200 ml of ether; the combined organic phases are then washed with 200 ml of a saturated aqueous solution of sodium chloride and dried and then evaporated to yield the expected compound.

Step B: 1a,23,7b-Tetrahydronaphtho[1,2-b]oxirene

To 27.5 g of the compound obtained in the Step above, dissolved in 180 ml of tetrahydrofuran, there is added dropwise, over 5 minutes, at ambient temperature, a solution of 10 g (180 mmol) of potassium hydroxide in 10 ml of water. After stirring for 5 days at ambient temperature, 200 ml of water are added and extraction is carried out with ethyl ether. The combined organic phases are washed and then dried. After evaporation, the product obtained is distilled in vacuo (approximately 0.1 mm Hg) in a Kugelrohr apparatus. The expected product distils at around 80° C.

Step C: tert-Butyl 4-[trans-2-hydroxy-1,2,3,4-tetrahydronaphth-1-yl]piperazine-1-carboxylate At ambient temperature, 4.4 g (30 mmol) of the compound obtained in the Step above and 5.6 g (30 mmol) of N-tert-butyloxycarbonylpiperazine in 60 ml of acetonitrile are mixed together and then heated at reflux for 40 hours. After evaporation and flash chromatography on 500 g of silica (eluant: dichloromethane/ethanol 98/2), the expected product is collected.

Step D: tert-Butyl 4-{trans-2-[(3,5-dibromobenzyl)oxy]-1,2,3,4-tetrahydronaphth-1-yl}piperazine-1-carboxylate At ambient temperature, to 0.44 g (11 mmol) of sodium hydride as a suspension in 20 ml of tetrahydrofuran there are added, over a few minutes, 3.3 g (10 mmol) of the compound obtained in the Step above, dissolved in 20 ml of tetrahydrofuran. The mixture is heated at 50° C. for 2 hours and there are then added, all at once, 3.3 g (10 mmol) of 3,5-dibromobenzyl bromide, and then 3.7 g (10 mmol) of tetra-n-butylammonium iodide, and heating is carried out overnight at 70° C. The mixture is then poured into 100 ml of water and extraction with two quantities, each of 100 ml, of ethyl ether is carried out. The combined organic phases are washed and dried. After evaporation and flash chromatography on 300 g of silica (eluant: dichloromethane 100%, and then dichloromethane/ethyl acetate 90/10), the expected compound is collected.

Step E: trans-1-{2-[(3,5-Dibromobenzyl)oxy]-1,2,3,4-tetrahydronaphth-1-yl}piperazine dihydrochloride Gaseous hydrogen chloride is bubbled through 5.8 g (10 mmol) of the above compound dissolved in 400 ml of ethyl acetate, at ambient temperature, for a few minutes. Stirring is then carried out for 3 hours at ambient temperature; the mixture is then concentrated by half (a precipitate appears) and 100 ml of ether are added; stirring is then carried out overnight at ambient temperature. After filtering off, rinsing and drying the precipitate, the expected compound is collected in racemic form.

Melting point (M.K.): 110-125° C.

EXAMPLE 16

(−) isomer of trans-1-{2-[(3,5-dibromobenzyl)oxy]-1,2,3,4-tetrahydro-naphth-1-yl}piperazine dihydrochloride After reconversion to the base, the racemic compound obtained in Example 15 is separated by preparative chiral HPLC chromatography on a CHIRALPAK AD column (eluant: acetonitrile/isopropanol/diethylamine 900/100/1). The first of the isomers thereby separated is converted into the hydrochloride salt using ethanolic HCl, and is then precipitated from ether. After filtering, rinsing and drying, the (−) enantiomer is obtained in an enantiomeric excess of more than 98%.

Melting point (M.K.): 113-126° C.

Optical rotation: $[\alpha] = -14.5$ (c=1%, MeOH, 20° C., $\lambda$=589 nm)

EXAMPLE 17

(+) isomer of trans-1-{2-[(3,5-dibromobenzyl)oxy]-1,2,3,4-tetrahydro-naphth-1-yl}piperazine dihydrochloride The second of the isomers separated in Example 16 is converted into a hydrochloride to yield the expected product.

Melting point (M.K.): 118-126° C.

Optical rotation: $[\alpha] = +14.4$ (c=1%, MeOH, 20° C., $\lambda$=589 nm)

EXAMPLE 18 trans-1-{2-[(3,5-Dibromobenzyl)oxy]-1,2,3,4-tetrahydronaphth-1-yl}-1,4-diazepane dihydrochloride Step A: tert-Butyl trans-4-[2-hydroxy-1,2,3,4-tetrahydronaphth-1-yl]-1,4-diazepane-1-carboxylate At ambient temperature, 3.0 g (20.5 mmol) of the compound obtained in Step B of Example 15 and 4.1 g (20.5 mmol) of N-tert-butyloxycarbonyl-homopiperazine in 41 ml of acetonitrile are mixed together and then heated at reflux for 48 hours. After evaporation and flash chromatography on 300 g of silica (eluant: dichloromethane/ethanol 98/2), the expected compound is collected.

Step B: tert-Butyl trans-4-{2-[(3,5-dibromobenzyl)oxy]-1,2,3,4-tetrahydronaphth-1-yl}-1,4-diazepane-1-carboxylate At ambient temperature, to 0.76 g (19 mmol) of sodium hydride as a suspension in 20 ml of tetrahydrofuran there are added, over a few minutes, 6.0 g (17.3 mmol) of the compound obtained in the Step above, dissolved in 50 ml of tetrahydrofuran. The mixture is heated at 50° C. for 2 hours and there are then added, all at once, 5.7 g (17.3 mmol) of 3,5-dibromo-benzyl bromide, and then 6.4 g (17.3 mmol) of tetra-n-butylammonium iodide, and heating is carried out overnight at 70° C. The mixture is then poured into 200 ml of water and extracted with ethyl ether. The combined organic phases are washed and dried. After evaporation and flash chromatography on 500 g of silica (eluant: dichloromethane 100%, then dichloromethane/ethyl acetate 95/5 and then dichloromethane/ethanol 95/5), the expected compound is collected.

Step C: trans-1-{2-[(3,5-Dibromobenzyl)oxy]-1,2,3,4-tetrahydronaphth-1-yl}-1,4-diazepane dihydrochloride Gaseous hydrogen chloride is gently bubbled through 4.9 g (8.2 mmol) of the compound obtained in the Step above, dissolved in 250 ml of ethyl acetate, at ambient temperature, for a few minutes. Stirring is carried out overnight at ambient temperature; the mixture is then concentrated by half (a precipitate appears) and stirring is carried out for a further 2 hours. After filtering off, rinsing and drying the precipitate, the expected compound is collected in racemic form.

Melting point (M.K.): 112-118° C.

EXAMPLE 19

(−) isomer of trans-1-{2-[(3,5-dibromobenzyl)oxy]-1,2,3,4-tetra-hydronaphth-1-yl}-1,4-diazepane dihydrochloride After reconversion to the base, the racemic compound obtained in Example 18 is separated by preparative chiral HPLC chromatography on a CHIRALPAK AD column (eluant: methanoudiethylamine 1000/1). The first of the isomers thereby separated is converted into the hydrochloride salt using ethanolic HCl. After filtration, rinsing and drying, the (−) enantiomer is obtained in an enantiomeric excess of more than 98%.

Melting point (M.K.): 122-126° C.

EXAMPLE 20

(+) isomer of trans-1-{2-[(3,5-dibromobenzyl)oxy]-1,2,3,4-tetra-hydronaphth-1-yl}-1,4-diazepane dihydrochloride The second of the isomers separated in Example 19 is converted into a hydrochloride to yield the expected product.

Melting point (M.K.): 119-140° C.

EXAMPLE 21

1-{(1S,2R)-2-[(3,5-Dibromobenzyl)oxy]-2,3-dihydro-1H-inden-1-yl}-piperazine dihydrochloride Step A: (1S,2R)-1-{4-[(4-Methylphenyl)sulphonyl]piperazin-1-yl}indan-2-ol To 8 g of (1S,2R)-1-aminoindan-2-ol (53.6 mmol) dissolved in 80 ml of dimethyl-formamide there are added 15 ml of triethylamine (107.2 mmol) and 15.8 g of N,N-bis(2-chloroethyl)-p-toluenesulphonamide (53.6 mmol). The mixture is heated at 80° C. for 24 hours and then the dimethylformamide is evaporated off. The residue is taken up in dichloromethane, washed, dried, filtered and evaporated. The oil obtained is purified by flash chromatography on silica (eluant: dichloromethane/ethyl acetate 95/5) to yield the expected product in the form of a meringue.

Step B: 1-{(1S,2R)-2-[(3,5-Dibromobenzyl)oxy]-2,3-dihydro-1H-inden-1-yl}-4-[(4-methylphenyl)sulphonyl]piperazine The expected product is obtained according to the procedure described in Step B of Example 1, starting from the compound obtained in the Step above.

Step C: 1-{(1S,2R)-2-[(3,5-Dibromobenzyl)oxy]-2,3-dihydro-1H-inden-1-yl}piperazine 1.1 g of the compound obtained in the Step above (1.77 mmol) are heated for 2 hours at 90° C. in the presence of 10 ml of a solution of HBr/acetic acid (33%) and 808 mg of 4-hydroxybenzoic acid (5.85 mmol). Cooling is carried out and NaOH (20%) is added until the pH=10; extraction with dichloromethane, drying, filtration and evaporation are then carried out. The oil obtained is purified by flash chromatography on 100 g of silica (eluant: dichloromethane/ethanol/ammonia 90/10/1) to yield the expected product in the form of a colourless oil.

Step D: 1-{(1S,2R)-2-[(3,5-Dibromobenzyl)oxy]-2,3-dihydro-1H-inden-1-yl}piperazine dihydrochloride To 1.2 g of the compound obtained in the Step above (2.57 mmol), dissolved in ethyl acetate, there are added, at ambient temperature, a 2M solution of hydrochloric acid in ether. The mixture is stirred for 30 minutes and then evaporated to dryness. The residue is crystallised from ethyl acetate, filtered and dried to yield the expected product (cis compound) in the form of white crystals.

Melting point (MK): 162-176° C.

Optical rotation $[\alpha]=-2.9$ (c=1%, MeOH, 20° C., $\lambda=589$ nm)

EXAMPLE 22

1-{(1R,2S)-2-[(3,5-Dibromobenzyl)oxy]-2,3-dihydro-1H-inden-1-yl}-piperazine dihydrochloride The expected product is obtained according to the procedure described in Example 21, starting from (1R,2S)-1-aminoindan-2-ol.

Melting point (MK): 142-150° C.

Optical rotation: $[\alpha]=+5.8$ (c=1%, MeOH, 20° C., $\lambda=589$ nm)

EXAMPLE 23 cis-1-{4-[(3,5-Dibromobenzyl)oxy]-2,3,4,5-tetrahydro-1-benzoxepin-5-yl}piperazine dihydrochloride Step A: tert-Butyl 4-(4-oxo-2,3,4,5-tetrahydro-1-benzoxepin-5-yl)piperazine-1-carboxylate At −78° C., 0.88 ml of oxalyl chloride (10 mmol) is poured into 25 ml of dichloromethane and then, at the same temperature, there are slowly added 1.02 ml of dimethyl sulphoxide (14.3 mmol). Stirring is carried out for 10 minutes at −78° C. 2.5 g (7.17 mmol) of the compound obtained in Step B of Example 8, dissolved in 15 ml of dichloromethane, are poured into the reaction mixture. Stirring is carried out for 15 minutes at −78° C. and there are then added, over 20 minutes, 5 ml (35.9 mmol) of triethylamine. The mixture is then allowed to return to 0° C. and the reaction mixture is then poured into 100 ml of ice-cold water. Extraction with dichloromethane, drying, filtration and evaporation to dryness are carried out to yield the expected product in the form of an oil.

Step B: tert-Butyl cis-4-(4-hydroxy-2,3,4,5-tetrahydro-1-benzoxepin-5-yl)piperazine-1-carboxylate To 2.4 g (6.93 mmol) of the compound obtained in the Step above, dissolved in 50 ml of methanol there are added, at 0° C. and in portions, 130 mg of NaBH$_4$ (3.5 mmol, 0.5 of an equivalent). Stirring is carried out for 1 hour at 0° C. and the methanol is then evaporated off. The residue obtained is taken up in toluene, washed, dried, filtered and evaporated. The residue obtained is purified by flash chromatography on silica (eluant: toluene/ethanol 95/5) to yield the expected product in the form of an oil.

Step C: cis-1-{4-[(3,5-Dibromobenzyl)oxy]-2,3,4,5-tetrahydro-1-benzoxepin-5-yl}-piperazine dihydrochloride The expected product is obtained according to the procedure described in Steps B and C of Example 1 starting from the compound obtained in the Step above.

Melting point (MK): 166-191° C.

EXAMPLE 24 cis-1-[2-((3,5-Dibromobenzyloxy)-1,2,3,4-tetrahydronaphth-1-yl}-piperazine dihydrochloride The expected product is obtained according to the procedure described in Example 23, starting from the compound obtained in Step C of Example 15.

Melting point (MK):155-159° C.

EXAMPLE 25 cis-1-{6-[(3,5-Dibromobenzyl)oxy]-6,7,8,9-tetrahydro-5H-benzo-[7]annulen-5-yl}piperazine dihydrochloride Step A: tert-Butyl 4-(6-oxo-6,7,8,9-tetrahydro-5H-benzo[7]annulen-5-yl)piperazine-1-carboxylate To 4.4 g (12.6 mmol) of the compound obtained in Step A of Example 7, dissolved in 44 ml of dimethyl sulphoxide, there are added, at ambient temperature, 8.8 g of stabilised 2-iodoxybenzoic acid (SIBX) (56.3 mmol, 4.4 equivalents). Stirring is carried out for 2 hours at 25° C., and the mixture is then poured into water. The insoluble material obtained is filtered off. The filtrate is extracted with ethyl acetate, dried, filtered and evaporated to dryness. The residue obtained is purified by flash chromatography on silica (eluant: dichloromethane/ethyl acetate 95/5) to yield the expected product.

Melting point (BK): 85-95° C.

Step B: tert-Butyl 4-(6-hydroxy-6,7,8,9-tetrahydro-5H-benzo[7]annulen-5-yl)piperazine-1-carboxylate 1.5 g (4.3 mmol) of the compound obtained in the Step above are treated according to the method described in Step B of Example 23. The yellow oil obtained is purified by flash chromatography on silica (eluant: dichloromethane/ethyl acetate 95/5) to yield the expected product in the form of a cis/trans mixture (cis/trans ratio=80/20).

Step C: tert-Butyl cis-4-{6-[(3,5-dibromobenzyl)oxy]-6,7,8,9-tetrahydro-5H-benzo-[7]annulen-5-yl}piperazine-1-carboxylate 650 mg of the compound obtained in the Step above (cis/trans=80/20) (1.87 mmol) are treated according to the method described in Step B of Example 1 to yield an oil which is purified by flash chromatography on silica (eluant: cyclohexane/ethyl acetate 95/5) to yield the expected product.

Step D: cis-1-{6-[(3,5-Dibromobenzyl)oxy]-6,7,8,9-tetrahydro-5H-benzo[7]annulen-5-yl}piperazine dihydrochloride 350 mg of the compound obtained in the Step above (0.58 mmol) are treated according to the method described in Step C of Example 1, and then the product obtained is crystallised from isopropyl ether to yield the expected product in the form of white crystals.

Melting point (MK): 149-158° C.

EXAMPLE 26 trans-3-[(3,5-Dibromobenzyl)oxy]-4-piperazin-1-ylchroman-6-carbonitrile dihydrochloride Step A: 6-Bromo-1a, 7b-dihydro-2H-oxireno[c]chromene 8.5 g of 6-bromo-2H-chromene (40.3 mmol) prepared according to the synthesis method described in J. Org. Chem., 1998, 63, 864 are treated according to the method described in Step A of Example 8 to yield the expected product in the form of an oil.

Step B: tert-Butyl trans-4-(6-bromo-3-hydroxy-3,4-dihydro-2H-chromen-4-yl)-piperazine-1-carboxylate 7.6 g of the compound obtained in the Step above (33.5 mmol) are treated according to the method described in Step A of Example 1. The residue obtained is purified by flash chromatography on silica (eluant: toluene/ethanol 95/5) to yield the expected product in the form of an oil.

Step C: tert-Butyl trans-4-(6-cyano-3-hydroxy-3,4-dihydro-2H-chromen-4-yl)piperazine-1-carboxylate 1 g of the compound obtained in the Step above (2.4 mmol) is dissolved in 10 ml of dimethylformamide. The solution is degassed using argon and there are then added 112 mg of tetrakis(triphenylphosphine)palladium(0) (0.09 mmol) and 170 mg of zinc cyanide (1.4 mmol). Heating is carried out at 80° C. for 3 days. The reaction mixture is then cooled and poured into water. The mixture is extracted with ethyl acetate, washed with water, dried, filtered and evaporated to dryness. The residue obtained is purified by flash chromatography on silica (eluant: dichloromethane/ethyl acetate 90/10) to yield the expected product in the form of an oil.

Step D: trans-3-[(3,5-Dibromobenzyl)oxy]-4-piperazin-1-ylchroman-6-carbonitrile dihydrochloride The expected product is obtained according to the procedure described in Steps B and C of Example 1, starting from the compound obtained in the Step above.

Melting point (MK): 185-200° C.

EXAMPLE 27 trans-7-[(3,5-Dibromobenzyl)oxy]-8-piperazin-1-yl-5,6,7,8-tetrahydronaphthalene-2-carbonitrile dihydrochloride Step A: 6-Bromo-1a,2,3,7b-tetrahydronaphtho[1,2-b]oxirene 7.4 g of the compound of Preparation A (35 mmol) are treated with Oxone® according to the method described in Step A of Example 8 to yield the expected product in the form of an oil.

Step B: tert-Butyl trans-4-(7-bromo-2-hydroxy-1,2,3,4-tetrahydronaphth-1-yl)-piperazine-1-carboxylate 6.5 g of tert-butyl piperazine-1-carboxylate (35 mmol) and 7.9 g of the compound obtained in the Step above (35 mmol) are dissolved in 45 ml of dimethylformamide, and the reaction mixture is then heated at 110° C. for 24 hours. After evaporation to dryness, there is obtained a residue which is purified by flash chromatography on silica (eluant: toluene/ethanol 98/2) to yield the expected product in the form of an oil.

Step C: tert-Butyl trans-4-(7-cyano-2-hydroxy-1,2,3,4-tetrahydronaphth-1-yl)-piperazine-1-carboxylate 4 g of the compound obtained in the Step above (9.7 mmol) are treated according to the method described in Step C of Example 26. Heating is carried out at 80° C. for 2 hours. The reaction mixture is then cooled and poured into water. The mixture is extracted with dichloromethane, washed with water, dried, filtered and evaporated to dryness. The residue obtained is purified by flash chromatography on silica (eluant: dichloromethane/ethanol 98/2) to yield the expected product in the form of an oil.

Step D: trans-7-[(3,5-Dibromobenzyl)oxy]-8-piperazin-1-yl-5,6,7,8-tetrahydro-naphthalene-2-carbonitrile dihydrochloride The expected product is obtained according to the procedure described in Steps B and C of Example 1, starting from the compound obtained in the Step above.

Melting point (MK): 169-191° C.

EXAMPLE 28 trans-4-[(3,5-Dibromobenzyl)oxy]-5-piperazin-1-yl-2,3,4,5-tetrahydro-1-benzoxepin-7-carbonitrile dihydrochloride Step A: 7-Bromo-1a,2,3,8b-tetrahydrooxireno[d][1]benzoxepin 4 g of the compound of Preparation B are treated with Oxone® according to the method described in Step A of Example 8 to yield the expected product in the form of an oil.

Step B: tert-Butyl trans-4-(7-bromo-4-hydroxy-2,3,4,5-tetrahydro-1-benzoxepin-5-yl)-piperazine-1-carboxylate 3.9 g of the compound obtained in the Step above (16.2 mmol) are treated according to the method described in Step A of Example 1. Heating is continued for a further 3 days. There is thereby obtained a residue which is purified by flash chromatography on silica (eluant: dichloromethane/ethanol 98/2) to yield the expected product in the form of an oil.

Step C: tert-Butyl trans-4-(7-cyano-4-hydroxy-2,3,4,5-tetrahydro-1-benzoxepin-5-yl)-piperazine-1-carboxylate 5.8 g of the compound obtained in the Step above (13.6 mmol) are treated according to the method described in Step C of Example 26. Heating is carried out at 80° C. for 20 hours. The reaction mixture is then cooled and poured into water. The mixture is extracted with dichloromethane, washed with water, dried, filtered and evaporated to dryness. The residue obtained is purified by flash chromatography on silica (eluant: toluene/ethanol 95/5) to yield the expected product in the form of an oil.

Step D: trans-4-[(3,5-Dibromobenzyl)oxy]-5-piperazin-1-yl-2,3,4,5-tetrahydro-1-benzoxepin-7-carbonitrile dihydrochloride The expected product is obtained according to the procedure described in Steps B and C of Example 1, starting from the compound obtained in the Step above.

Melting point (MK): 163-195° C.

EXAMPLE 29 trans-5-[(4-{2-[(3,5-Dibromobenzyl)oxy]-2,3-dihydro-1H-inden-1-yl}piperazin-1-yl)methyl]-2,4-dihydro-3H-1,2,4-triazol-3-one dihydrochloride Step A: trans-5-[(4-{2-[(3,5-Dibromobenzyl)oxy]-2,3-dihydro-1H-inden-1-yl}piperazin-1-yl)methyl]-2,4-dihydro-3H-1,2,4-triazol-3-one After reconversion to the base, the compound obtained in Step C of Example 1 (2.14 mmol) is dissolved in 30 ml of dimethylformamide. There are added 0.75 ml (4.28 mmol) of diisopropylethylamine and 314 mg (2.35 mmol) of 5-(chloromethyl)-2,4-dihydro-3H-1,2,4-triazol-3-one prepared according to the method described in Tetrahedron Letters, 2000, 41, 8661. The mixture is stirred for 12 hours at ambient temperature and then evaporated to dryness. The residue obtained is taken up in dichloromethane, washed, dried, filtered and evaporated. The oil obtained is purified by flash chromatography on silica to yield the expected product.

Step B: trans-5-[(4-{2-[(3,5-Dibromobenzyl)oxy]-2,3-dihydro-1H-inden-1-yl}piperazin-1-yl)methyl]-2,4-dihydro-3H-1,2,4-triazol-3-one dihydrochloride 800 mg of the compound obtained in the Step above (1.42 mmol) are dissolved in 50 ml of ethyl acetate. 2.8 ml (5.68 mmol) of a 2M solution of hydrochloric acid in ether are then added. After stirring for 30 minutes at ambient temperature, the mixture is evaporated to dryness and the residue is crystallised from acetonitrile to yield the expected product.

Melting point (MK): 198-202° C.

EXAMPLE 30 trans-1-{2-[(3,5-Dibromobenzyl)oxy]-2,3-dihydro-1H-inden-1-yl}-4-[(2S)-2,3-dihydro-1,4-benzodioxin-2-ylmethyl]piperazine dihydrochloride Step A: tert-Butyl 4-[(2R)-2,3-dihydro-1,4-benzodioxin-2-ylcarbonyl]piperazine-1-carboxylate 5 g of (2R)-2,3-dihydro-1,4-benzodioxin-2-carboxylic acid (27.8 mmol) are dissolved in 300 ml of acetonitrile. 6 g of N,N'-dicyclohexylcarbodiimide (29.1 mmol) and then 4.1 g of 1-hydroxybenzotriazole (30.6 mmol) are added. Finally, 6.2 g of tert-butyl piperazine-1-carboxylate (33.4 mmol) are added and stirring is carried out for 12 hours at ambient temperature. The reaction mixture is subsequently filtered and the filtrate is then evaporated to dryness. The oil thereby obtained is purified by flash chromatography on silica (eluant: toluene/ethyl acetate 80/20) to yield the expected product in the form of an oil.

Step B: tert-Butyl 4-[(2S)-2,3-dihydro-1,4-benzodioxin-2-ylmethyl]piperazine-1-carboxylate 500 mg of the compound obtained in the Step above (1.44 mmol) are dissolved in 5 ml of anhydrous tetrahydrofuran. There are then added dropwise, at ambient temperature, 4.4 ml (4.3 mmol) of a 1M solution of borane in tetrahydrofuran. The mixture is heated at reflux for 2 hours, cooled, hydrolysed slowly using 5 ml of ethanol, and evaporated to dryness. The residue obtained is crystallised from water, filtered and dried to yield the expected product.

Melting point (BK)=97-99° C.

Step C: 1-[(2S)-2,3-Dihydro-1,4-benzodioxin-2-ylmethyl]piperazine dihydrochloride 7.5 g of the compound obtained in the Step above (22.4 mmol) are stirred for 2 days, at ambient temperature, in the presence of 100 ml of a 2.6N solution of hydrochloric acid in ethanol. The crystals formed are filtered off and dried to yield the expected product in the form of a white solid.

Melting point (BK)=166-172° C.

Step D: trans 1-{4-[(2S)-2,3-Dihydro-1,4-benzodioxin-2-yl-methyl]piperazin-1-yl}indan-2-ol To 1.6 g (6.8 mmol) of 1-[(2S)-2,3-dihydro-1,4-benzodioxin-2-ylmethyl]piperazine, obtained by reconverting the compound of the above Step to the base, dissolved in 10 ml of acetonitrile, there are added 1.08 g of indene oxide (8.16 mmol). The reaction mixture is heated at 80° C. for 30 hours and then evaporated to dryness. The oil thereby obtained is purified by flash chromatography on silica (eluant: dichloromethane/ethanol/ammonia 90/10/1) to yield the expected compound in the form of a meringue.

Step E: trans-1-{2-[(3,5-Dibromobenzyl)oxy]-2,3-dihydro-1H-inden-1-yl}-4-[(2S)-2,3-dihydro-1,4-benzodioxin-2-yl-methyl]piperazine The expected product is obtained according to the procedure described in Step B of Example 1, starting from the compound obtained in the Step above.

Step F: trans-1-{2-[(3,5-Dibromobenzyl)oxy]-2,3-dihydro-1H-inden-1-yl}-4-[(2S)-2,3-dihydro-1,4-benzodioxin-2-yl-methyl]piperazine dihydrochloride To 210 mg of the compound obtained in the Step above (0.34 mmol), dissolved in 20 ml of ethyl acetate, there are added, at ambient temperature, 0.5 ml (1 mmol) of a 2M solution of hydrochloric acid in ether. After stirring for 30 minutes, the reaction mixture is evaporated to dryness. The residue obtained is crystallised from ethyl acetate, filtered and dried to yield the expected product in the form of white crystals.

Melting point (MK): 137-145° C.

EXAMPLE 31

(+)-cis-1-{(1S,2R)-2-[(3,5-Dibromobenzyl)oxy]-2,3-dihydro-1H-inden-1-yl}-4-(pyridin-2-ylcarbonyl)piperazine dihydrochloride Step A: cis-1-{(1S,2R)-2-[(3,5-Dibromobenzyl)oxy]-2,3-dihydro-1H-inden-1-yl}-4-(pyridin-2-ylcarbonyl)piperazine To 263 mg of pyridine-2-carboxylic acid (2.14 mmol), dissolved in 10 ml of tetrahydro-furan, there are added 382 mg of carbonyldiimidazole (2.35 mmol, 1.1 equivalents) and then, after stirring for 3 hours at ambient temperature, a solution of 1 g (2.14 mmol) of the compound obtained in Step C of Example 21 in 20 ml of tetrahydrofuran. Stirring for 12 hours at 25° C., and then addition of water, extraction with dichloromethane, drying, filtration and evaporation to dryness are carried out. The oil obtained is purified by flash chromatography on silica (eluant: dichloromethane/ethanol 95/5) to yield the expected product in the form of an oil.

Step B: cis-1-{(1S,2R)-2-[(3,5-Dibromobenzyl)oxy]-2,3-dihydro-1H-inden-1-yl}-4-(pyridin-2-ylcarbonyl)piperazine dihydrochloride 900 mg of the compound obtained in the Step above (1.57 mmol) are treated according to the method described in Step F of Example 30. The solid obtained is filtered off and dried to yield the expected product in the form of white crystals.

Melting point (MK): 108-122° C.

Optical rotation: [α]=+27.3 (c=1%, methanol, 20° C., λ=589 nm)

EXAMPLE 32

1-(trans-2-{1-[3,5-Bis(trifluoromethyl)phenyl]ethoxy}-1,2,3,4-tetra-hydronaphth-1-yl)piperazine dihydrochloride, diastereoisomer 1

Step A: tert-Butyl 4-(trans-2-{[3,5-bis(trifluoromethyl)benzoyl]oxy}-1,2,3,4-tetra-hydronaphth-1-yl)piperazine-1-carboxylate To 11.7 g (35.2 mmol) of the compound obtained in Step C of Example 15 and 5.9 ml (42.2 mmol) of triethylamine, dissolved in 300 ml of dichloromethane, there are added, at ambient temperature, 7.05 ml (38.7 mmol) of bis(trifluoromethyl)benzoyl chloride in 50 ml of dichloromethane, dropwise over 1 hour 10 minutes, and then 0.5 g of dimethylamino-pyridine. The reaction mixture is then heated at reflux for 5 days, and then a further 1.3 ml of the acid chloride are added and refluxing is continued for 20 hours. After evaporation of the medium, the residue obtained is filtered over 200 g of silica (eluant: dichloromethane) to yield the expected product.

Step B: tert-Butyl 4-[trans-2-({1-[3,5-bis(trifluoromethyl)phenyl]vinyl}oxy)-1,2,3,4-tetrahydronaphth-1-yl]piperazine-1-carboxylate To 13.2 g (23 mmol) of the compound obtained in the Step above in 92 ml of tetrahydro-furan there are added, at ambient temperature, 46 ml of a 1M solution of dicyclopentadienyldimethyltitanium in toluene, and the reaction mixture is heated at 85° C. for 20 hours. A further 23 ml of the 1M solution of dicyclopentadienyldimethyltitanium in toluene are added, dropwise, at 85° C. over 10 minutes, and then heating at that temperature is continued for a further 24 hours. The mixture is allowed to cool, 500 ml of pentane are added; the mixture is filtered over Celite and rinsed with pentane until the filtrate is colourless. After evaporation of all the combined filtrates and flash chromatography on 800 g of silica (eluant: dichloromethane, and then dichloromethane/ethyl acetate 98/2), the expected product is obtained.

Step C: tert-Butyl 4-(trans-2-{1-[3,5-bis(trifluoromethyl)phenyl]ethoxy}-1,2,3,4-tetrahydronaphth-1-yl)piperazine-1-carboxylate 8.34 g (14.6 mmol) of the compound obtained in the Step above, dissolved in 150 ml of ethanol, are hydrogenated at ambient temperature and atmospheric pressure for 7 hours in the presence of 1 g of 5% palladium-on-carbon. After filtration over Celite, rinsing with ethanol and evaporation, the expected product is obtained in the form of a non-quantifiable and non-separable mixture of diastereoisomers.

Step D: 1-(trans-2-{1-[3,5-Bis(trifluoromethyl)phenyl]ethoxy}-1,2,3,4-tetrahydronaphth-1-yl)piperazine dihydrochloride, diastereoisomer 1

Gaseous hydrogen chloride is gently bubbled through 8.4 g (14.6 mmol) of the compound obtained in the Step above, dissolved in 500 ml of ethyl acetate, at ambient temperature for a few minutes. Stirring overnight at ambient temperature and then evaporation to dryness are carried out. The residue is dissolved in 100 ml of water and, with vigorous stirring, is converted to the base using 8 g of sodium carbonate. The paste which precipitates out is extracted twice using 100 ml of dichloromethane each time. The combined organic phases are dried and concentrated, and the residue obtained is chromatographed on 700 g of silica (eluant: dichloromethane/ethanol/ammonia 95/5/0.5) to yield the first diastereoisomer, which is converted to the dihydrochloride by the action of ethereal HCl. After crystallisation from pentane, the expected product is obtained.

Melting point (M.K.): 98-102° C.

EXAMPLE 33

1-(trans-2-{1-[3,5-Bis(trifluoromethyl)phenyl]ethoxy}-1,2,3,4-tetra-hydronaphth-1-yl)piperazine dihydrochloride, diastereoisomer 2

The second product eluted in Step D of Example 32 yields the second diastereoisomer, which is converted to the dihydrochloride.

Melting point (M.K.): 98-101° C.

EXAMPLE 34

1-[(1S,2R)-2-Benzyloxy-2,3-dihydro-1H-inden-1-yl]piperazine dihydrochloride

The expected product (cis compound) is obtained according to the procedure of Example 21, replacing the 3,5-dibromobenzyl bromide in Step B by benzyl bromide.

Melting point: 104-125° C.

EXAMPLE 35 trans-1-{2-[(3,5-Dimethylbenzyl)oxy]-2,3-dihydro-1H-inden-1-yl}-piperazine dihydrochloride The expected product is obtained according to the procedure described in Steps D and E of Example 15, starting from the compound obtained in Step A of Example 1 and 3,5-dimethylbenzyl bromide.

Melting point: 161-70° C.

EXAMPLE 36

1-[(1S,2R)-2-[(3,5-Difluorobenzyl)oxy]-2,3-dihydro-1H-inden-1-yl]-piperazine dihydrochloride The expected product (cis compound) is obtained according to the procedure of Example 21, replacing the 3,5-dibromobenzyl bromide in Step B by 3,5-difluorobenzyl bromide.

Melting point: 160-190° C.

EXAMPLE 37

1-[(1S,2R)-2-Benzyloxy-2,3-dihydro-1H-inden-1-yl]-4-methyl-piperazine dihydrochloride The expected product is obtained by N-methylation of the compound of Example 34.

Melting point: 182-189° C.

EXAMPLE 38

1-[(1S,2R)-2-[(3,5-Dimethylbenzyl)oxy]-2,3-dihydro-1H-inden-1-yl]-piperazine dihydrochloride Step A: 1-{(1S,2R)-2-[(3,5-Dimethylbenzyl)oxy]-2,3-dihydro-1H-inden-1-yl}-4-[(4-methylphenyl)sulphonyl]piperazine The expected product is obtained according to the procedure described in Steps A and B of Example 21, replacing the 3,5-dibromobenzyl bromide in Step B by 3,5-dimethylbenzyl bromide.

Step B: 1-{(1S,2R)-2-[(3,5-Dimethylbenzyl)oxy]-2,3-dihydro-1H-inden-1-yl}piperazine 3 g of sodium (130 mmol) are added to a solution of 3.6 g of naphthalene (28 mmol) in 30 ml of 1,2-dimethoxyethane. The reaction mixture is stirred at ambient temperature for 2 hours to form the sodium/naphthalene/1,2-dimethoxyethane solution. 14.8 ml (64 mmol) of the resulting solution are added, at a temperature of −70° C., to a solution of 3 g (6.1 mmol) of the compound obtained in the Step above in 55 ml of 1,2-dimethoxyethane. The colour of the solution changes from white to blue. Stirring is carried out for 30 minutes at −70° C., followed by hydrolysis using 100 ml of water. The mixture is then extracted with ethyl acetate, dried, filtered and evaporated to dryness. The residue obtained is purified by flash chromatography on 200 g of silica (eluant: dichloromethane/ethanol/ammonia 90/10/1) to yield the expected product in the form of an oil.

Step C: 1-{(1S,2R)-2-[(3,5-Dimethylbenzyl)oxy]-2,3-dihydro-1H-inden-1-yl}piperazine dihydrochloride 3.6 ml (7.16 mmol, 2 equivalents) of a 2M solution of ethereal hydrogen chloride are added to 1.2 g (3.58 mmol) of the compound obtained in the Step above in 50 ml of acetonitrile. Crystallisation is initiated by scratching, and then stirring is carried out for 15 minutes at ambient temperature. The white crystals obtained are dried to yield the expected product.

Melting point: 170-193° C.

EXAMPLE 39 trans-1-{2-[(3,5-Difluorobenzyl)oxy]-2,3-dihydro-1H-inden-1-yl}-piperazine dihydrochloride The expected product is obtained according to the procedure of Example 1, replacing the 3,5-dibromobenzyl bromide in Step B by 3,5-difluorobenzyl bromide.

Melting point: 185-198° C.

EXAMPLE 40 trans-1-(2-{[3,5-Bis(trifluoromethyl)benzyl]oxy}-2,3-dihydro-1H-inden-1-yl)piperazine dihydrochloride The expected product is obtained according to the procedure of Example 1, replacing the 3,5-dibromobenzyl bromide in Step B by 3,5-bis(trifluoromethyl)benzyl bromide.

Melting point: 140-160° C.

EXAMPLE 41 trans-1-{2-[(3,5-Dibromobenzyl)oxy]-6-methoxy-2,3-dihydro-1H-inden-1-yl}piperazine dihydrochloride The expected product is obtained according to the procedure of Example 4, replacing the 2H-chromene in Step A by 5-methoxy-1H-indene.

Melting point: 184-195° C.

EXAMPLE 42 trans-1-{2-[(3,5-Dichlorobenzyl)oxy]-6-methoxy-2,
3-dihydro-1H-inden-1-yl}piperazine dihydrochloride The expected product is obtained according to the procedure of Example 4, starting from 5-methoxy-1H-indene and 3,5-dichlorobenzyl bromide.

Melting point: 169-176° C.

EXAMPLE 43 trans-1-{2-[(3,5-Dichlorobenzyl)oxy]-2,3-dihydro-
1H-inden-1-yl}-piperazine dihydrochloride The expected product is obtained according to the procedure of Example 1, replacing the 3,5-dibromobenzyl bromide in Step B by 3,5-dichlorobenzyl bromide.

Melting point: 115-127° C.

EXAMPLE 44 trans-1-{3-[(3,5-Dichlorobenzyl)oxy]-3,4-dihydro-
2H-chromen-4-yl}-piperazine dihydrochloride The expected product is obtained according to the procedure of Example 4, replacing the 3,5-dibromobenzyl bromide in Step D by 3,5-dichlorobenzyl bromide.

Melting point: 110-118° C.

EXAMPLE 45 trans-1-{2-[(3,5-Bis(trifluoromethyl)benzyl)oxy]-1,
2,3,4-tetrahydro-naphth-1-yl}piperazine dihydrochloride The expected product is obtained according to the procedure of Example 15, replacing the 3,5-dibromobenzyl bromide in Step D by 3,5-bis(trifluoromethyl)benzyl bromide.

Melting point (MK): 98-101° C.

EXAMPLE 46 trans-1-{3-[3-Fluoro-5-(trifluoromethyl)benzyloxy]-
3,4-dihydro-2H-chromen-4-yl}piperazine dihydrochloride The expected product is obtained according to the procedure of Example 4, replacing the 3,5-dibromobenzyl bromide in Step D by 3-fluoro-5-(trifluoromethyl)benzyl bromide.

Melting point: 102-113° C.

EXAMPLE 47 trans-1-{3-(3-Chloro-5-fluorobenzyloxy)-3,4-dihydro-2H-chromen-4-yl}piperazine dihydrochloride Step A: tert-Butyl trans-4-{3-[(3-chloro-5-fluorobenzyl)oxy]-3,4-dihydro-2H-chromen-4-yl}piperazine-1-carboxylate The expected product is obtained according to the procedure described in Steps A to D of Example 4, replacing the 3,5-dibromobenzyl bromide in Step D by 3-chloro-5-fluorobenzyl bromide.

Step B: trans-1-{3-(3-Chloro-5-fluorobenzyloxy)-3,4-dihydro-2H-chromen-4-yl}-piperazine dihydrochloride The expected product is obtained according to the procedure described in Step C of Example 1, starting from the compound obtained in the Step above.

Melting point: 90-95° C.

EXAMPLE 47 bis trans-1-{3-(3-Chloro-5-fluorobenzyloxy)-3,4-dihydro-2H-chromen-4-yl}piperazine dimethanesulphonate The expected product is obtained by reaction of the compound of Example 47 with sodium hydroxide, followed by conversion of the product thereby obtained into a salt using methanesulphonic acid.

Melting point: 161-171° C.

EXAMPLE 48 cis-4-[2-(3,5-Dibromobenzyloxy)-1,2,3,4-tetrahydronaphth-1-yl]-morpholine hydrochloride The expected product is obtained according to the procedure of Example 23, replacing, in Step A, the compound obtained in Step B of Example 8 by the compound obtained in Step B of Example 10.

Melting point: 195-198° C.

EXAMPLE 49 trans-4-{3-[(3,5-Dibromobenzyl)oxy]-3,4-dihydro-
2H-chromen-4-yl}morpholine hydrochloride The expected product is obtained according to the procedure described in Steps B to D of Example 10, starting from the compound obtained in Step B of Example 4.

Melting point: 143-148° C.

EXAMPLE 50 trans-4-{2-[(3,5-Dibromobenzyl)oxy]-1,2,3,4-tetrahydro-1-naphthyl}-piperidine hydrochloride Step A: 1-(4-Pyridyl)-1,2,3,4-tetrahydro-1-naphthol 85 ml of a 1.5M solution of n-butyllithium in hexane are added, dropwise, to a solution of 20 g of 4-bromopyridine in 73 ml of ether, cooled to −78° C. Stirring is carried out for 30 minutes at that temperature, a solution of 1-tetralone in 73 ml of ether is then poured in and, at the end of the addition, the mixture is allowed to return to ambient temperature. After stirring overnight, a saturated aqueous solution of ammonium chloride is poured in. After separation, extraction with ether is carried out. The ethereal phases are combined and extracted with 1N hydrochloric acid. The combined acid phases are adjusted to pH=8 using 20% sodium hydroxide solution and extracted with dichloromethane. After drying, the expected product is isolated, which is purified by high-speed chromatography on silica (eluant: dichloromethane/methanol 95/5) to yield the expected product.

Melting point (B.K.)=160-162° C.

Step B: 4-(3,4-Dihydro-1-naphthyl)pyridine 2 g of the compound obtained in the Step above, 10 ml of water and 10 ml of sulphuric acid 95% are mixed together, heated at 80° C. for 30 minutes, cooled to 0° C. and adjusted to pH=10 using 20% sodium hydroxide solution. The mixture is extracted with dichloromethane, washed with water, dried and evaporated to yield the expected product.

Step C: 4-(2,3-Dihydronaphtho[1,2-b]oxiren-7b(1aH)-yl) pyridine 1-oxide

At a temperature of from 20 to 25° C., a solution containing 5.4 g of the product obtained in the Step above, 20 g of sodium bicarbonate, 35 ml of acetone, 20 ml of water and 200 ml of ethyl acetate is poured into a solution of 29.3 g of Oxone® in 200 ml of water. Stirring overnight at ambient temperature, dilution with water and extraction with ethyl acetate are carried out. After conventional treatment, the expected product is isolated.

Step D: 1-(1-Oxido-4-pyridyl)-1,2,3,4-tetrahydro-2-naphthol

To a solution of 450 mg of the product obtained in the Step above in 10 ml of anhydrous tetrahydrofuran, in the presence of a trace of Bromocresol Green, there are added, all at once and at ambient temperature, 289 mg of sodium cyanoborohydride. Boron trifluoride etherate is added until the coloured indicator turns yellow and as many times as necessary in the course of the reaction to maintain the pH at 4-5. At the end of the reaction, concentrated hydrochloric acid is added until the pH=1, and stirring is carried out for 30 minutes at ambient temperature. The mixture is adjusted to pH=8 using sodium hydroxide solution and extracted with ethyl acetate, and after treatment the expected product is isolated (80% trans, 20% cis).

Step E: 1-(4-Piperidyl)-1,2,3,4-tetrahydro-2-naphthol 1.78 g of the product obtained in the Step above, 1 g of platinum oxide, 0.75 ml of concentrated hydrochloric acid and 75 ml of ethanol are mixed in a reactor and hydrogenated under a pressure of 1 bar. After reacting for 6 hours at ambient temperature, filtration is carried out; 8 ml of sodium hydroxide solution are added, the ethanol is evaporated off, a minimum amount of water is used for dissolution and the pH is adjusted to 10. After extraction and conventional treatment, the expected product is obtained (80% trans, 20% cis).

Step F: tert-Butyl 4-(2-hydroxy-1,2,3,4-tetrahydro-1-naphthyl)-1-piperidinecarboxylate A solution of 2.1 g of di(tert-butyl)dicarbonate in 50 ml of dichloromethane is added to 2.06 g of the product obtained in the Step above, dissolved in 50 ml of dichloromethane. Stirring is carried out for two hours at ambient temperature, followed by evaporation to dryness. After purification on silica (eluant: dichloromethane/methanol 95/5), the expected product is isolated (80% trans, 20% cis).

Step G: tert-Butyl 4-{2-[(3,5-dibromobenzyl)oxy]-1,2,3,4-tetrahydro-1-naphthyl}-1-piperidinecarboxylate 241 mg of sodium hydride 60% in oil are introduced into a solution of 1.9 g of the compound obtained in the Step above in 20 ml of anhydrous tetrahydrofuran, cooled to 0° C. Stirring is carried out for 15 minutes and there are then added, still at that temperature, 20 mg of tetrabutylammonium iodide and finally 1.9 g of 3,5-dibromobenzyl bromide. The mixture is allowed to return to ambient temperature and is stirred for 24 hours. The mixture is evaporated to dryness, taken up in water and dichloromethane and, after conventional treatment and chromatography on silica (eluant: dichloromethane), the expected product is isolated in the form of a white meringue (80% trans, 20% cis).

Step H: trans-4-{2-[(3,5-Dibromobenzyl)oxy]-1,2,3,4-tetrahydro-1-naphthyl}piperidine hydrochloride 2 g of the compound obtained in the Step above, in 20 ml of ethanol, are treated with 19 ml of a 3.6N solution of ethanolic hydrogen chloride. After 24 hours, the precipitate formed is filtered off, rinsed and dried to yield the expected product in the form of the hydrochloride. (The cis compound is in the filtrate).

Melting point: 152-167° C.

EXAMPLE 51 cis-1-Acetyl-3-[(3,5-dibromobenzyl)oxy]-4-(1-piperazinyl)-1,2,3,4-tetrahydroquinoline dihydrochloride Step A: 1-Acetyl-1,2-dihydroquinoline 23.43 g of sodium borohydride are introduced, in portions, into a solution of 20 g of quinoline in 200 ml of acetic acid and 77.5 ml of acetic anhydride, cooled to 0° C. The mixture is then heated for 2 hours at 60° C. and is stirred overnight at ambient temperature. The mixture is concentrated, diluted with water, adjusted to pH=10 with sodium hydroxide solution and extracted with ether. The combined ethereal phases are washed with 1N hydrochloric acid and then at neutral pH and after conventional treatment the expected product is isolated.

Step B: 3-Acetyl-1a,2,3,7b-tetrahydrooxireno[2,3-c]quinoline

The expected product is obtained according to the procedure described in Step A of Example 8, starting from the compound obtained in the Step above.

Step C: tert-Butyl trans-4-[1-acetyl-3-hydroxy-1,2,3,4-tetrahydro-4-quinolyl]-1-piperazinecarboxylate The expected product is obtained according to the procedure described in Step A of Example 1, starting from the compound obtained in the Step above.

Step D: cis-1-Acetyl-3-[(3,5-dibromobenzyl)oxy]-4-(1-piperazinyl)-1,2,3,4-tetrahydroquinoline dihydrochloride The expected product is obtained according to the procedure of Example 23, starting from the compound obtained in the Step above.

Melting point: 164-167° C.

EXAMPLE 52 trans-1-{3-[(3,5-Dibromobenzyl)oxy]-3,4-dihydro-2H-chromen-4-yl}-N-methyl-4-piperidinamine dihydrochloride Step A: tert-Butyl trans-1-{3-[(3,5-dibromobenzyl)oxy]-3,4-dihydro-2H-chromen-4-yl}-N-methyl-4-piperidylcarbamate 0.2 g of sodium hydride (60% in oil) is added to 1 g of the compound obtained in Step B of Example 9 and 0.42 ml of methyl iodide in 10 ml of tetrahydrofuran, maintaining the temperature of the reaction mixture at 0° C. After 15 minutes at that temperature, the mixture is stirred for 48 hours at ambient temperature, diluted with water and extracted with ethyl acetate. After conventional treatment, the expected product is isolated.

Step B: trans-1-{3-[(3,5-Dibromobenzyl)oxy]-3,4-dihydro-2H-chromen-4-yl}-N-methyl-4-piperidinamine dihydrochloride The expected product is obtained according to the procedure described in Step C of Example 1, starting from the compound obtained in the Step above.
Melting point: 192-195° C.

EXAMPLE 53 trans-1-{3-[(3,5-Dibromobenzyl)oxy]-3,4-dihydro-2H-chromen-4-yl}-N,N-dimethyl-4-piperidinamine dihydrochloride Step A: trans-1-{3-[(3,5-Dibromobenzyl)oxy]-3,4-dihydro-2H-chromen-4-yl}-N-methyl-4-piperidinamine The expected product is obtained by reconverting the compound of Example 52 to the base.

Step B: trans-1-{3-[(3,5-Dibromobenzyl)oxy]-3,4-dihydro-2H-chromen-4-yl}-N,N-dimethyl-4-piperidinamine The expected product is obtained according to the procedure described in Step A of Example 52, starting from the compound obtained in the Step above.

Step C: trans-1-{3-[(3,5-Dibromobenzyl)oxy]-3,4-dihydro-2H-chromen-4-yl}-N,N-dimethyl-4-piperidinamine dihydrochloride The expected product is obtained by conversion of the compound obtained in the Step above into a salt using hydrochloric acid.
Melting point: 187-190° C.

EXAMPLE 54 trans-1-{3-[(3,5-Dimethoxybenzyl)oxy]-3,4-dihydro-2H-chromen-4-yl}piperazine dihydrochloride The expected product is obtained according to the procedure of Example 4, replacing the 3,5-dibromobenzyl bromide in Step D by 3,5-dimethoxybenzyl bromide.
Melting point: 108-115° C.

EXAMPLE 55 trans-1-{3-Benzyloxy-3,4-dihydro-2H-chromen-4-yl}piperazine dihydrochloride

The expected product is obtained according to the procedure of Example 4, replacing the 3,5-dibromobenzyl bromide in Step D by benzyl bromide.
Melting point: 66-80° C.

EXAMPLE 56 trans-1-{3-[(3-Fluorobenzyl)oxy]-3,4-dihydro-2H-chromen-4-yl}-piperazine dihydrochloride The expected product is obtained according to the procedure of Example 4, replacing the 3,5-dibromobenzyl bromide in Step D by 3-fluorobenzyl bromide.
Melting point: 180-184° C.

EXAMPLE 57 trans-1-{3-[(3-Chlorobenzyl)oxy]-3,4-dihydro-2H-chromen-4-yl}-piperazine dihydrochloride The expected product is obtained according to the procedure of Example 4, replacing the 3,5-dibromobenzyl bromide in Step D by 3-chlorobenzyl bromide.
Melting point: 97-107° C.

EXAMPLE 58 trans-1-{3-[(3,4-Dichlorobenzyl)oxy]-3,4-dihydro-2H-chromen-4-yl}-piperazine dihydrochloride The expected product is obtained according to the procedure of Example 4, replacing the 3,5-dibromobenzyl bromide in Step D by 3,4-dichlorobenzyl bromide.
Melting point: 114-121° C.

EXAMPLE 59 trans-1-{2-[(3-Chloro-5-fluorobenzyl)oxy]-2,3-dihydro-1H-inden-1-yl}piperazine dimethanesulphonate Step A: trans-1-{2-[(3-Chloro-5-fluorobenzyl)oxy]-2,3-dihydro-1H-inden-1-yl}-piperazine dihydrochloride The expected product is obtained according to the procedure described in Steps B and C of Example 1, replacing the 3,5-dibromobenzyl bromide in Step B by 3-chloro-5-fluorobenzyl bromide.

Step B: trans-1-{2-[(3-Chloro-5-fluorobenzyl)oxy]-2,3-dihydro-1H-inden-1-yl}-piperazine dimethanesulphonate The expected product is obtained by reconverting the compound obtained in the Step above to the base, followed by conversion into a salt using methanesulphonic acid.
Melting point: 175-182° C.

EXAMPLE 60 trans-1-{3-[(3-(Trifluoromethyl)benzyl)oxy]-3,4-dihydro-2H-chromen-4-yl}piperazine dimethanesulphonate Step A: trans-1-{3-[(3-(Trifluoromethyl)benzyl)oxy]-3,4-dihydro-2H-chromen-4-yl}-piperazine dihydrochloride The expected product is obtained according to the procedure of Example 4, replacing the 3,5-dibromobenzyl bromide in Step D by 3-(trifluoromethyl)benzyl bromide.

Step B: trans-1-{3-[(3-(Trifluoromethyl)benzyl)oxy]-3,4-dihydro-2H-chromen-4-yl}-piperazine dimethanesulphonate The expected product is obtained by reconverting the compound obtained in the Step above to the base, followed by conversion into a salt using methanesulphonic acid.
Melting point: 123-127° C.

EXAMPLE 61 trans-1-{3-[(3-Cyanobenzyl)oxy]-3,4-dihydro-2H-chromen-4-yl}-piperazine dimethanesulphonate Step A: trans-1-{3-[(3-Cyanobenzyl)oxy]-3,4-dihydro-2H-chromen-4-yl}piperazine dihydrochloride The expected product is obtained according to the procedure of Example 4, replacing the 3,5-dibromobenzyl bromide in Step D by 3-cyanobenzyl bromide.

Step B: trans-1-{3-[(3-Cyanobenzyl)oxy]-3,4-dihydro-2H-chromen-4-yl}piperazine dimethanesulphonate The expected product is obtained by reconverting the compound obtained in the Step above to the base, followed by conversion into a salt using methanesulphonic acid.

Melting point: 118-121° C.

EXAMPLE 62

(+) isomer of trans-1-{3-(3-chloro-5-fluorobenzyloxy)-3,4-dihydro-2H-chromen-4-yl}piperazine dibenzoyltartrate (+)

Step A: (+) isomer of tert-butyl trans-4-(3-[(3-chloro-5-fluorobenzyl)oxy]-3,4-dihydro-2H-chromen-4-ylpiperazine-1-carboxylate The expected compound is obtained by separation, by means of preparative chiral HPLC chromatography, of the racemic mixture obtained in Step A of Example 47.

Step B: (+) isomer of trans-1-{3-(3-chloro-5-fluorobenzyloxy)-3,4-dihydro-2H-chromen-4-yl}piperazine dihydrochloride The expected product is obtained according to the procedure described in Step C of Example 1, starting from the compound obtained in the Step above.

Step C: (+) isomer of trans-1-{3-(3-chloro-5-fluorobenzyloxy)-3,4-dihydro-2H-chromen-4-yl}piperazine dibenzoyltartrate (+)

The expected product is obtained by reconverting the compound obtained in the Step above to the base, followed by conversion into a salt using (+)-dibenzoyltartaric acid.

Melting point: 100-107° C.

EXAMPLE 63

(−) isomer of trans-1-{3-(3-chloro-5-fluorobenzyloxy)-3,4-dihydro-2H-chromen-4-yl}piperazine dibenzoyltartrate (−)

Step A: (−) isomer of tert-butyl trans-4-{3-[(3-chloro-5-fluorobenzyl)oxy]-3,4-dihydro-2H-chromen-4-yl}piperazine-1-carboxylate The expected compound is the second of the enantiomers separated in Step A of Example 62.

Step B: (−) isomer of trans-1-{3-(3-chloro-5-fluorobenzyloxy)-3,4-dihydro-2H-chromen-4-yl}piperazine dihydrochloride The expected product is obtained according to the procedure described in Step C of Example 1, starting from the compound obtained in the Step above.

Step C: (−) isomer of trans-1-{3-(3-chloro-5-fluorobenzyloxy)-3,4-dihydro-2H-chromen-4-yl}piperazine dibenzoyltartrate (−)

The expected product is obtained by reconverting the compound obtained in the Step above to the base, followed by conversion into a salt using (−)-dibenzoyltartaric acid.

Melting point: 100-107° C.

EXAMPLE 64 trans-1-{3-[(3,5-Difluorobenzyl)oxy]-3,4-dihydro-2H-chromen-4-yl}piperazine dimethanesulphonate Step A: trans-1-{3-[(3,5-Difluorobenzyl)oxy]-3,4-dihydro-2H-chromen-4-yl}piperazine dihydrochloride The expected product is obtained according to the procedure of Example 4, replacing the 3,5-dibromobenzyl bromide in Step D by 3,5-difluorobenzyl bromide.

Step B: trans-1-{3-[(3-Difluorobenzyl)oxy]-3,4-dihydro-2H-chromen-4-yl}piperazine dimethanesulphonate The expected product is obtained by reconverting the compound obtained in the Step above to the base, followed by conversion into a salt using methanesulphonic acid.

Melting point: 178-182° C.

EXAMPLE 65 trans-4-{3-[(3,5-Dibromobenzyl)oxy]-3,4-dihydro-2H-chromen-4-yl}-piperidine hydrochloride The expected product is obtained according to the procedure of Example 50, replacing, in Step A, 1-tetralone by 2,3-dihydro-4H-chromen-4-one.

Melting point: 148-167° C.

EXAMPLE 66 trans-1-{3-[(3-(Trifluoromethoxy)benzyl)oxy]-3,4-dihydro-2H-chromen-4-yl}piperazine dimethanesulphonate Step A: trans-1-{3-[(3-(Trifluoromethoxy)benzyl)oxy]-3,4-dihydro-2H-chromen-4-yl}piperazine dihydrochloride The expected product is obtained according to the procedure of Example 4, replacing the 3,5-dibromobenzyl bromide in Step D by 3-(trifluoromethoxy)benzyl bromide.

Step B: trans-1-(3-[(3-(Trifluoromethoxy)benzyl)oxy]-3,4-dihydro-2H-chromen-4-ylpiperazine dimethanesulphonate The expected product is obtained by reconverting the compound obtained in the Step above to the base, followed by conversion into a salt using methanesulphonic acid.

Melting point: 132-135° C.

Pharmacological Study of Compounds of the Invention

EXAMPLE 67

Determination of the Affinity for Serotonin Reuptake Sites in the Rat

The affinity of the compounds for the serotonin (5-HTT) reuptake site is evaluated by competition experiments with [$^3$H]-citalopram on rat frontal cortex membranes. The cortices are homogenised using a Polytron in 40 volumes (weight/volume) of cold Tris-HCl (50 mM, pH 7.4) incubation buffer containing 120 mM NaCl and 5 mM KCl and are then centrifuged for a first time. The sediment is resuspended in the same buffer, incubated for 10 minutes at 37° C. and then re-centrifuged. The membranes are washed a further two times and the sediment is then resuspended in an appropriate volume of incubation buffer. The membranes are then incubated for 2 hours at 25° C. with the compound under test in the presence of 0.7 nM [³H]-citalopram. Non-specific binding is determined with 10 µM fluoxetine. At the end of the incubation period, the samples are filtered through Unifilter GF/B type filters pretreated with PEI (0.5%) and washed several times with the incubation buffer. The radioactivity retained on the filters is counted after addition of scintillation liquid, with the aid of a scintillation counter. The isotherms obtained are analysed by non-linear regression to determine the $IC_{50}$ values, which are converted into $K_i$ using the Cheng-Prusoff equation:

$$K_i = IC_{50}/(1+L/k_D)$$

wherein L represents the concentration of radioligand and $k_D$ is the dissociation constant of [³H]-citalopram on the serotonin reuptake site (0.7 nM). The results are expressed as $pK_i = -\log K_i$.

The results obtained for representative compounds of the invention are collated in the following table:

| Compound | $pK_i$ r5-HTT |
|---|---|
| Example 1 | 8.35 |
| Example 4 | 7.10 |
| Example 21 | 7.91 |
| Example 36 | 8.97 |
| Example 38 | 8.73 |
| Example 42 | 7.71 |
| Example 44 | 7.31 |
| Example 47 | 7.45 |

EXAMPLE 68

$hnK_1$ Binding

The affinity of compounds of the invention was determined by competition experiments in the presence of [³H]-Substance P (Sar-9, MetO2-11,2-propyl-3,4-3H). IM9 human lymphoblast cells endogenously expressing $NK_1$ receptors are centrifuged and taken up in the incubation buffer containing 50 mM TRIS, 150 mM NaCl, 4 mM $CaCl_2$, protease inhibitors at $1/100^e$ (Cocktail SIGMA P8340) and 0.2% BSA. The volume of incubation buffer is determined so as to obtain a concentration of $5 \times 10^6$ cells/ml. The cell preparation is then incubated together with 1.5 nM [³H]-Substance P and the compound under test for 90 minutes at ambient temperature. Non-specific binding is determined in the presence of 1 µM GR 205171.

At the end of the incubation period, the samples are filtered through Unifilter GF/B type filters pretreated with PEI (0.1%) and washed several times with the filtration buffer (50 mM TRIS, 150 mM NaCl, 4 mM $CaCl_2$). The radioactivity retained on the filters is measured by counting after addition of scintillation liquid to the filters. The counts are analysed by non-linear regression, allowing the isotherms to be plotted and the $IC_{50}$ values to be determined. The latter are then converted into inhibition constants ($K_i$) by means of the Cheng-Prusoff equation:

$$K_i = IC_{50}/(1+L/K_D)$$

wherein L is the concentration of [³H]-Substance P and $K_D$ is the dissociation constant of [³H]-Substance P for human $NK_1$ receptors (0.53 nM). The results are expressed as $pK_i(-\log K_i)$.

The results obtained for representative compounds of the invention are collated in the following table:

| Compound | $pK_i$ $NK_1$ |
|---|---|
| Example 1 | 6.84 |
| Example 4 | 8.25 |
| Example 7 | 8.14 |
| Example 8 | 7.54 |
| Example 9 | 7.96 |
| Example 13 | 6.60 |
| Example 15 | 7.48 |
| Example 19 | 7.40 |
| Example 40 | 6.85 |

EXAMPLE 69

Pharmaceutical composition

Formula for the preparation of 1000 tablets each containing 10 mg of active ingredient:

| | |
|---|---|
| Compound of Example 1 | 10 g |
| Hydroxypropylcellulose | 2 g |
| Wheat starch | 10 g |
| Lactose | 100 g |
| Magnesium stearate | 3 g |
| Talc | 3 g |

The invention claimed is:

1. A compound selected from those of formula (I):

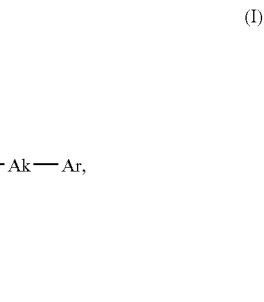

wherein:
  $R_1$, $R_2$, $R_3$ and $R_4$, which may be the same or different, each represent an atom or group selected from hydrogen, halogen, linear or branched $C_1$-$C_6$alkyl, linear or branched $C_1$-$C_6$alkoxy, phenyl and cyano,
  X represents a bond, an oxygen atom or a group selected from —$(CH_2)_m$—, —$OCH_2$— and —$NR_5$—,
  m represents 1 or 2,
  $R_5$ represents a hydrogen atom or a group selected from linear or branched $C_1$-$C_6$alkyl, $COR_6$ and $CO_2R_6$,
  $R_6$ represents a linear or branched $C_1$-$C_6$alkyl group,
  Y represents $NR_7$,
  $R_7$ represents a hydrogen atom or a group selected from $COR_9$ and linear or branched $C_1$-$C_6$alkyl, the alkyl group being optionally substituted by a 5-oxo-4,5-dihydro-1H-1,2,4-triazol-3-yl or 2,3-dihydro-1,4-benzodioxin-2-yl group,
  $R_9$ represents a group selected from linear or branched $C_1$-$C_6$alkyl and aryl,
  Z represents a nitrogen atom,
  n represents 2,
  Ak represents a linear or branched $C_1$-$C_6$alkylene chain,
  Ar represents an aryl group, its optical isomers, and addition salts thereof with a pharmaceutically acceptable acid, it being understood that an aryl group means phenyl, biphenylyl or naphthyl, each of the groups optionally being substituted by one or more identical or different groups selected from halogen, linear or branched $C_1$-$C_6$alkyl, linear or branched $C_1$-$C_6$alkoxy, hydroxy, cyano, linear or branched $C_1$-$C_6$trihaloalkyl and linear or branched $C_1$-$C_6$trihaloalkoxy.

2. The compound of claim 1, wherein Y represents NH.

3. The compound of claim 1, wherein X represents a bond, an oxygen atom or a group selected from —OCH$_2$— and —(CH$_2$)$_m$— wherein m represents 1 or 2.

4. The compound of claim 1, which is selected from trans-1-{2-[(3,5-dibromobenzyl)oxy]-1,2,3,4-tetrahydronaphth-1-yl}-1,4-diazepane, and enantiomers, and addition salts thereof with a pharmaceutically acceptable acid.

5. A pharmaceutical composition comprising as active ingredient a compound of claim 1, in combination with one or more pharmaceutically acceptable, inert, non-toxic carriers.

6. A method for treating a living animal body, including a human, afflicted with a condition selected from depressive states, comprising the step of administering to the living animal body, including a human, an amount of a compound of claim 1 which is effective for alleviation of the condition.

* * * * *